US012320754B2

(12) United States Patent
Tong et al.

(10) Patent No.: US 12,320,754 B2
(45) Date of Patent: Jun. 3, 2025

(54) DEVICES AND METHODS FOR DETECTING OR MONITORING THE QUALITY OF FOOD PRODUCTS

(71) Applicants: University of Florida Research Foundation, Inc., Gainesville, FL (US); Georgia Tech Research Corporation, Atlanta, GA (US)

(72) Inventors: Zhaohui Tong, Gainesville, FL (US); Hanxi Bao, Gainesville, FL (US); Guanghui Lan, Atlanta, GA (US); Karyn E. Moses, Gainesville, FL (US)

(73) Assignees: University of Florida Research Foundation, Inc., Gainesville, FL (US); Georgia Tech Research Corporation, Atlanta, GA (US)

( * ) Notice: Subject to any disclaimer, the term of this patent is extended or adjusted under 35 U.S.C. 154(b) by 932 days.

(21) Appl. No.: 17/189,624

(22) Filed: Mar. 2, 2021

(65) Prior Publication Data
US 2021/0279857 A1 Sep. 9, 2021

Related U.S. Application Data

(60) Provisional application No. 62/984,481, filed on Mar. 3, 2020.

(51) Int. Cl.
*G01N 21/80* (2006.01)
*G01N 21/77* (2006.01)

(52) U.S. Cl.
CPC ..... *G01N 21/80* (2013.01); *G01N 2021/7796* (2013.01); *G01N 2201/129* (2013.01);
(Continued)

(58) Field of Classification Search
CPC .......... E06B 3/2632; G01N 2021/7796; G01N 21/80; G01N 2201/129; G01N 33/12; G06T 2207/10024; G06T 2207/30128
See application file for complete search history.

(56) References Cited

U.S. PATENT DOCUMENTS

| 4,187,383 A | 2/1980 | Cowherd, III et al. |
| 2018/0284092 A1 * | 10/2018 | Tong ..................... B65D 81/34 |

FOREIGN PATENT DOCUMENTS

| CN | 108805246 A | * 11/2018 | ....... G06K 19/06037 |
| JP | 201635390 A | * 3/2016 | ............. G01N 21/80 |

OTHER PUBLICATIONS

Tarjan ("A readability analysis for QR code application in a traceability system") Computers and Electronics in Agriculture, vol. 109, 2014, pp. 1-11, ISSN 0168-1699, (Year: 2014).*

(Continued)

*Primary Examiner* — Jennifer Wecker
*Assistant Examiner* — Jonathan Bortoli
(74) *Attorney, Agent, or Firm* — Thomas | Horstemeyer, LLP

(57) ABSTRACT

Described herein are devices for determining or monitoring the quality of a food product. In one aspect, the devices comprise a pH-sensitive film incorporated within a quick response code, wherein the pH-sensitive film is positioned to be in contact with the food product. The pH-sensitive film produces different colors subject to changes in pH of the food product. The color produced by the pH-sensitive film can then be correlated to the quality of the food product. The quick response code can provide additional information regarding the food product.

20 Claims, 10 Drawing Sheets

(52) U.S. Cl.
CPC ............... *G06T 2207/10024* (2013.01); *G06T 2207/30128* (2013.01)

(56) References Cited

OTHER PUBLICATIONS

Moradi ("A novel pH-sensing indicator based on bacterial cellulose nanofibers and black carrot anthocyanins for monitoring fish freshness"), Carbohydrate Polymers, vol. 222, (Year: 2019).*
CN-108805246-A English translation (Year: 2024).*
JP201635390A English translation (Year: 2025).*

* cited by examiner pH 2.8 - 10

DEVICES AND METHODS FOR DETECTING OR MONITORING THE QUALITY OF FOOD PRODUCTS

CROSS REFERENCE TO RELATED APPLICATIONS

This application claims priority upon U.S. provisional application Ser. No. 62/984,481 filed on Mar. 3, 2020. This application is hereby incorporated by reference in its entirety.

STATEMENT REGARDING FEDERALLY SPONSORED RESEARCH OR DEVELOPMENT

This invention was made with government support under 2017-68005-26807 awarded by The United States Department of Agriculture, National Institutes of Food & Agriculture, NIFA. The government has certain rights in the invention.

BACKGROUND

Food spoilage is an unresolved food safety issue currently faced by the food industry. It was reported that the food spoilage caused approximately 50% waste of our food before and after it reached to the customers (Parfitt et al., 2010) due to the delay in food spoilage detection. Sensory and microbiological analyses are common methods to determine the shelf life of foods or spoilage under storage (Ellis & Goodacre, 2001). Sensory method (e.g. polymerase chain reaction (PCR) is a common analysis in most meat plants but requires 10-20 hours for complete analysis (Scheu et al., 1998). Direct monitoring of microorganisms using techniques such as total viable counts (TVC) is accurate, but expensive and time consuming (requiring 5-7 days for analysis) (Ellis & Goodacre, 2001). The rapid detection methods such as volatile organic compounds (VOCs) detected by mass spectroscopy and epifluorescent microscopy (Dainty, 1996; Pacquit et al., 2007) have been developed, but these methods need to know the specific organisms that caused the food spoilage. All these methods are unattractive and unsatisfactory to predict individual batches and monitor remaining shelf life under storage or display. There is a great need of a method that can rapidly detect food spoilage and immediately inform the consumers or retailers.

SUMMARY

Described herein are devices and methods for determining or monitoring the quality of a food product. In one aspect, the devices comprise a pH-sensitive film incorporated within a quick response code, wherein the pH-sensitive film is positioned to be in contact with the food product. The pH-sensitive film produces different colors subject to changes in pH of the food product. The color produced by the pH-sensitive film can then be correlated to the quality of the food product. The quick response code can provide additional information regarding the food product.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 3 shows the use of a device described herein for food quality classification.

DETAILED DESCRIPTION

Figure 1:
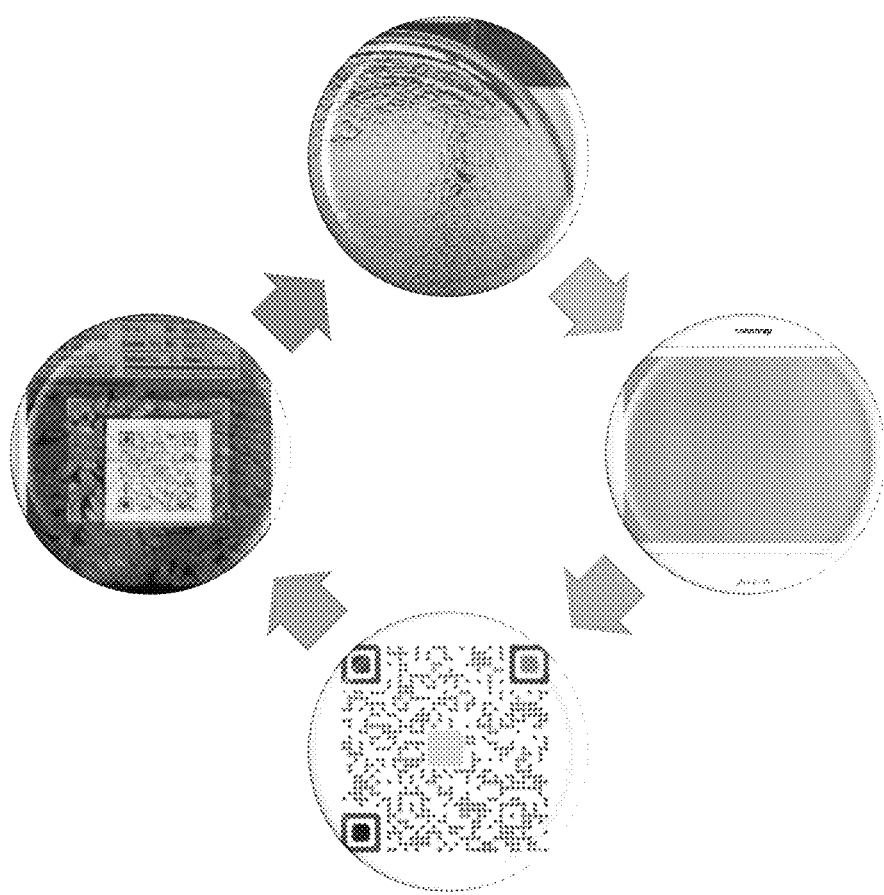
FIG. 1 shows a pH-responsive film sensor with the color verification for the spoilage indication of perishable food.

Before the present materials, articles and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a solvent" includes mixtures of two or more solvents and the like.

"Optional" or "optionally" means that the subsequently described event or circumstance can or cannot occur, and that the description includes instances where the event or circumstance occurs and instances where it does not.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, the term "about" is used to provide flexibility to a numerical range endpoint by providing that a given numerical value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

As used herein, the term "admixing" is defined as mixing two or more components together so that there is no chemical reaction or physical interaction. The term "admixing" also includes the chemical reaction or physical interaction between the two or more components.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1-about 3, from 1 to about 3, from about 1 to 3, etc., as well as 1, 2, 3, 4, and 5, individually. The same principle applies to ranges reciting only one numerical value as a minimum or maximum. The ranges should be interpreted as including endpoints (e.g., when a range of "from about 1 to 3" is recited, the range includes both of the endpoints 1 and 3 as well as the values in between). Furthermore, such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed, that while specific reference to each various individual combination and permutation of these compounds may not be explicitly disclosed, each is specifically contemplated and described herein. For example, if a pH-sensitive film is disclosed and discussed, and a number of different quick response codes are discussed, each and every combination of pH-sensitive film and quick response code that is possible is specifically contemplated unless specifically indicated to the contrary. For example, if a class of pH-sensitive films A, B, and C are disclosed, as well as a class of quick response codes D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such composition is specifically contemplated and should be considered disclosed.

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The term "small molecule", as used herein, generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

The term "polymer", as used herein, is used as generally understood in the literature and refers to a macromolecule made from many repeat units covalently bonded together. The polymer can be a "homopolymer" meaning it is made entirely of one type of repeat unit, optionally having different end-groups, including capped or acidic end groups. The polymer can be a "copolymer", meaning a single polymeric material that is comprised of two or more different types of monomers. The copolymer can be of any form, including random, block, and graft copolymers. The copolymers can have any end-group, including capped or acid end groups. The polymer can be linear or branched. The polymer can be characterized by a degree of polymerization that can be either a number-averaged degree of polymerization or a weight-average degree of polymerization. The polymer can have a degree of polymerization that is on the order of 100, 1,000, or even 10,000; for example the polymer can have a degree of polymerization that is about 50, 100, 150, 200, 250, 500, 750, 1,000, 1,500, 2,000, 3,000, 4,000, 5,000, 10,000 or greater. The polymer can have a degree of polymerization that is up to about 80,000, 60,000, 50,000, 40,000, 30,000, 25,000, 20,000, or less. The polymer can be characterized by an average molecular weight, e.g. a weight-averaged molecular weight or a number-average molecular weight. The polymer can have a variety of molecular weights depending upon the size of the repeat units and the degree of polymerization. The polymer can have a molecular weight of about 500 g/mol to 10,000,000 g/mol, about 800 g/mol to 1,000,000 g/mol, about 1,000 g/mol to 1,000,000 g/mol, about 2,000 g/mol to 1,000,000 g/mol, about 2,000 g/mol to 500,000 g/mol, about 2,000 g/mol to 250,000 g/mol, about 2,000 g/mol to 200,000 g/mol, about 2,000 g/mol to 100,000 g/mol, or about 5,000 g/mol to 50,000 g/mol.

The term "oligomer", as used herein, refers to a larger molecule formed from more than one repeat unit covalently bonded in a manner analogous to a polymer but that is still not large enough to be considered a polymer. Oligomers will typically have from a few to tens of repeat units, for example about 2, 3, 4, 5, 6, 7, 8, 9, 10, or more repeat units. Oligomers can have about 80, 60, 50, 40, 30, 25, 20, 18, 17, 16, 15, or fewer repeat units. The oligomer can have a molecular weight from The term "dendrimer", as used herein, refers to a larger molecule or oligomer having a highly branched structure of 1, 2, 3, 4, or more branched arms extending from and attached to, either directly or through a linking moiety, one or more chemically addressable cores. A dendrimer can be symmetric around the core, and can adopt a spherical three-dimensional morphology. The dendrimer can be monodisperse. The dendrimer can be characterized by the "generation", referring to the number of layers or successive branches extending from the core to the surface along an arm of the dendrimer. The dendrimer can have a generation of 1, 2, 3, 4, 5, 6, or more. For a dendrimer synthesized via regular, sequential addition of branched layers, the generation can refer to the number of distinct addition steps. The term dendrimer can include a "dendron", meaning a dendrimer having branches emanating from a single core, either directly or through a linking moiety, to form a dendrimer.

The term "monodisperse", as used herein, refers to a population of particles (e.g., oligomers, dendrimers, or polymers) wherein the particles have substantially identical size and shape. A "monodisperse" population of particles can mean that at least about 60%, 70%, 80%, 90%, 95%, 99%, 99.5%, or more of the particles fall within a specified particle size range that is within plus or minus about 25%, 20%, 15%, 10%, 5%, 3%, 2%, 1%, or less of the root-mean-square (rms) size of the particles in the population.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The terms "active agent", as used herein, includes, without limitation, substances that act to detect, prevent, inhibit, or otherwise slow the progression of spoilage or of a food spoilage microorganism when applied to a surface or to a substance such as a food product.

The term "antimicrobial agent", as sued herein, refers to an agent destroys, inhibits or prevents the propagation, growth and multiplication of unwanted microbial organisms.

The term "microbial organisms" or "microbes" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Non-limiting examples of microbial organisms that can be controlled using the formulations and methods described herein include bacteria from the genus *Aeromonas* (e.g. *A. hydrophilia*), Arcobacter, *Bacillus* (e.g. *B. cereus*), *Brochothrix* (e.g. *B. thermosphacta*), *Campylobacter* (e.g. *C. jejuni*), *Carnobacterium* (e.g. *C. piscicola*), Chlostridium (e.g. *C. perfringens, C botulinum*), Enterobacteriacae, *Escherichia* (e.g. *E. coli* O157: H7), *Listeria* (e.g. *L. monocytogenes*), *Pseudomonas* (e.g. *P. putida, P. fluorescens*), *Salmonella* (e.g. *S. Typhimurium*), *Serratia* (e.g. *S. liquefaciens*), *Shigella, Staphylococcus* (e.g. *S. aureus*), *Vibrio* (e.g. *V. parahaemolyticus, V. cholerae*) and *Yersina* (e.g. *Y. enterocolitica*); fungi such as *Aspergillus* flavum and *Penicillium chrysogenum*; parasites such as Amoebiasis (*Emoebiasis histolytica*), Balantidiosis (*Balantidiosis coli*), *Entamoeba histolytica, Cyclospora* Cryptosporidiosis (e.g. *Cryptosporidium parvum*), Cyclosporidiosis (e.g. *cayetanensis*), Giardiasis (e.g. *Giardia lamblia, Giardia intestinalis*), Isosporiasis (*Isosporiasis belli*), Microsporidiosis (Enter ocytozoon bieneusi, *S. intestinalis*), *Trichinella spiralis* and *Toxoplasma gondii*. The term microbial organism also refers to vegetative or dormant forms of bacteria and fungi, such as spores wherein activation of the growth cycle may be controlled using the methods provided herein.

The terms "spoilage micro-organism" and "spoilage microbial organism", as used interchangeably herein refer to a micro-organism that acts to spoil food. Spoilage microorganisms may grow and proliferate to such a degree that a food product is made unsuitable or undesirable for human or animal consumption. The production of undesirable by-products by the microorganism, such as carbon dioxide, methane, nitrogenous compounds, butyric acid, propionic acid, lactic acid, formic acid, sulfur compounds, and other gases and acids can cause detrimental effects on the foodstuff alteration of the color of meat surfaces to a brown, grey or green color, or creation of an undesirable odor. The color and odor alterations of food products due to the growth of spoilage micro-organisms frequently result in the product becoming unfit for sale or consumption.

The term "pathogenic micro-organism" as used herein refers to a micro-organism capable of causing disease or illness in an animal or a human, for example, by the production of endotoxins, or by the presence of a threshold level of micro-organisms to cause food poisoning, or other undesirable physiological reactions in humans or animals.

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The terms "sufficient" and "effective", as used interchangeably herein, refer to an amount (e.g. mass, volume, dosage, concentration, and/or time period) needed to achieve one or more desired result(s). For example, a diagnostically effective amount refers to an amount needed to achieve one or more diagnostic effects or to indicate the occurrence of a diagnostic criteria.

Biodegradable polymers can include polymers that are insoluble or sparingly soluble in water that are converted chemically or enzymatically in the body into water-soluble materials. Biodegradable polymers can include soluble polymers crosslinked by hydolyzable cross-linking groups to render the crosslinked polymer insoluble or sparingly soluble in water. Biodegradable polymers in the conjugate can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethylmethacrylate), poly(butylmethacrylate), poly (isobutylmethacrylate), poly(hexlmethacrylate), poly (isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof.

The term "food products", as used herein, is to be understood in a broad sense and includes meat products, fish products, dairy products, beverage products, baking products, unpasteurized food products, salads, and sauces, marinades, salsas and seasonings. In some embodiments, the food product contains one or more meat products such as beef, pork, poultry, or fish. The food products can be ready-to-eat food products. The term "ready-to-eat" means the food product is distributed to be consumed without further preparation by the consumer or distributed to not require cooking or preparation to achieve food safety prior to consumption.

The term "meat product", as used herein, includes any food product that primarily contains animal tissue, e.g. contains at least 70%, at least 80%, at least 90%, or at least 95% animal tissue including, but not limited to, beef, pork, poultry, and fish. Other animal tissues can include the tissue of many ungulates that can be used for human consumption such as deer, oxen, antelope, sheep, and goat. The term "meat product" as used herein encompasses processed meats (such as sausages, hamburgers, luncheon meats and cold cuts) and pre-prepared meat dishes such as meat pies, fish pies, game pies, stews, lasagnas and other meat-containing pasta dishes, chicken kiev, chicken cordon-bleu, chicken-a-la-king, meat rolls, meatloaf, pates, sushi, sashimi, salmon mousses, fishcakes, stir-fries etc. The term "ready-to-eat meat product" should include any meat product, which is distributed to be consumed without further preparation by the consumer or distributed to not require cooking prior to consumption. Ready-to-eat meat products include, but are not limited to, pates, hot dogs, bologna, ham, salami, sausages, deli meats, cold cuts, and dried or cured meat products. Ready-to-eat meat products can include ready-to-eat beef products, ready-to-eat pork products, ready-to-eat poultry products, and ready-to-eat fish products.

The term "beef product", as used herein, refers to any food that primarily contains cow tissue, e.g. contains at least 70%, at least 80%, at least 90%, or at least 95% cow tissue. The term "cow" refers to any animal of the genus *Bos*, such as for example the *Bos Taurus*, which is used as a food source for human consumption. Exemplary cow breeds used as commercial livestock include the Holstein, Ayrshire, Angus, and Limousin.

The term "poultry product", as used herein, refers to any food that primarily contains poultry tissue, e.g. contains at least 70%, at least 80%, at least 90%, or at least 95% poultry tissue. The term "poultry" refers to any edible birds such as chickens, turkeys, ducks, geese, and squab. Poultry can include animals of the genus *Gallus*, for example the *Gallus gallus domesticus*, which is used as a food source for human consumption. Poultry can include animals of the genus *Meleagris*, for example the *Meleagris gallopavo*, which is used as a food source for human consumption.

The term "pork product", as used herein, refers to any food product that primarily contains pig tissue, e.g. contains at least 70%, at least 80%, at least 90%, or at least 95% pig tissue. The term "pig" refers to any animal of the genus *Sus*, such as for example *Sus Scrofa*, which is used as a food source for human consumption. Exemplary pig breeds used as commercial livestock include Berkshire, Large White, Duroc, Hampshire, Landrace, Meishan, Pietrain, and many others.

As used herein, the term "fish product" should include any food product that primarily contains tissue from an aquatic animal, e.g. contains at least 70%, at least 80%, at least 90%, or at least 95% tissue from an aquatic animal. Aquatic animals can include lobster, crab, fresh water fish, smoked salmon, smoked other fish, salted fish, saltwater fish and other seafood.

As used herein, the term "dairy product" should include any food product made using milk or milk products, including, but not limited to, milk, yogurt, ice cream, cheese, skimmed milk, acidified milk, butter milk, condensed milk, spreads, margarines, milk powder, butter, EMC (Enzyme Modified Cheese), dulche de leche, coffee whitener; coffee creamer, cream, sour cream, ghee, and dairy analogue. Cheese may be any cheese, e.g. fresh cheese, hard cheese, curd cheese, cream cheese, white mold cheese, blue mold cheese and process cheese.

As used herein, the term "unpasteurized food product" should include any food product, whereby at least one ingredient is unpasteurized and which undergoes no final heat treatment.

As used herein, an "effective amount" is at least the minimum concentration required to have the desired effect, e.g. the minimum concentration required to indicate the presence of a detectable level of one or more microorganisms or the minimum concentration required to cause a measurable decrease in the growth rate of one or more microorganisms or a measurable decrease in the amount of one or more microorganisms. An effective amount can substantially prevent the growth of one or more microorganisms for a period of time up to about 5 days, 7 days, 10 days, 14 days, 21 days, 25 days, 30 days, or 45 days.

The term "safe", as used herein with reference to food, refers to a state wherein the food is sufficiently free of pathogenic micro-organisms or the toxic products of microbial growth to be fit for human or animal consumption.

As used herein, the term "shelf life" refers to the period of time that a food product remains saleable to retail customers and remains fit and safe for use or consumption. Changes including, but not limited to, oxidation, odor development, discoloration in addition to microbial changes can alter the shelf life of the food product. In traditional meat processing, the shelf life of fresh meat and meat by-products is about 30 to 40 days after an animal has been slaughtered. Refrigeration of meat during this period of time largely arrests and/or retards the growth of microorganisms. Microorganisms present on meat products may have proliferated to a great extent and/or have generated unacceptable levels of undesirable by-products. Spoilage microorganisms may also act to discolor meat, making such meat unappealing and undesirable for human consumption. Pathogenic microorganisms may have proliferated in this time period to a level wherein they can cause disease in an animal that consumes the food product.

As used herein, the term "usable life" refers to the period of time that a high-pressure processed food product remains fit for human consumption, e.g. safe and substantially free of food spoilage, after having been removed from the original packaging. For example, deli-style ready-to-eat meat products may be opened and sliced at the deli counter. The unsliced meat at the deli counter will have a usable life different from the sliced deli meat. The usable life will depend upon factors such as the storage temperature, the surface area, and the handling conditions.

"Food spoilage", as used herein, refers to organoleptic changes in the food, i.e. alterations in the condition of food which makes it less palatable, for example, changes in taste, smell, texture or appearance which are related to contamination of the food with one or more spoilage microorganisms. Spoiled food may or may not be safe for consumption.

"Food preservation", as used herein, refers to methods which maintain or enhance food safety for example, by controlling the growth and proliferation of pathogenic and spoilage micro-organisms, thus guarding against food poisoning and delaying or preventing food spoilage. Food preservation helps food remain safe for consumption for longer periods of time (i.e. improves the shelf life) and inhibits or prevents nutrient deterioration and/or organoleptic changes which cause food to become less palatable.

The term "neutral pH," as used herein refers to a pH of about 6.8 to 7.2, about 6.9 to 7.1, about 6.95 to 7.05, or about 7.0.

The term "chemical stability", as generally used herein, refers to the ability of the nanoparticles to resist degradation via chemical pathways, such as oxidation, deamidation, or hydrolysis and/or to contain the contents of the nanoparticle for an extended period without substantially releasing the contents. A nanoparticle formulation is typically considered chemically stable if about 25%, 20%, 15%, 10%, 5%, or less of the components are degraded or if less than about 25%, 20%, 15%, 10%, 5%, or 1% of the contents of the nanoparticle are released after 1, 2, 3, 6, 9, 12, 24 months at about room temperature, e.g. about 20° C. to 25° C.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, and $C_3$-$C_{30}$ for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

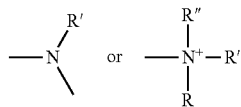

wherein R, R', and R" each independently represent a hydrogen, an alkyl, an alkenyl, —(CH$_2$)$_m$—R$_c$ or R and R' taken together with the N atom to which they are attached complete a heterocycle having from 4 to 8 atoms in the ring structure; R$_c$ represents an aryl, a cycloalkyl, a cycloalkenyl, a heterocycle or a polycycle; and m is zero or an integer in the range of 1 to 8. In preferred embodiments, only one of R or R' can be a carbonyl, e.g., R, R' and the nitrogen together do not form an imide. In still more preferred embodiments, the term "amine" does not encompass amides, e.g., wherein one of R and R' represents a carbonyl. In even more preferred embodiments, R and R' (and optionally R") each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

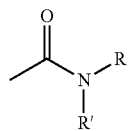

wherein R and R' are as defined above.

"Aryl", as used herein, refers to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro [2,3 b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-tetrahydroisoquinolinyl, quinolizinyl, quinoxalinyl, quinuclidinyl, tetrahydrofuranyl, tetrahydroquinolinyl, tetrazolyl, 6H-1,2,5-thiadiazinyl, 1,2,3-thiadiazolyl, 1,2,4-thiadiazolyl, 1,2,5- thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group). The term "aralkyloxy" can be represented by —O-aralkyl, wherein aralkyl is as defined above.

The term "carbocycle", as used herein, refers to an aromatic or non-aromatic ring(s) in which each atom of the ring(s) is carbon.

"Heterocycle" or "heterocyclic", as used herein, refers to a monocyclic or bicyclic structure containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocycle, an aromatic or heteroaromatic moiety, —$CF_3$, —CN, or the like.

The term "carbonyl" is art-recognized and includes such moieties as can be represented by the general formula:

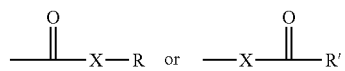

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid". Where X is an oxygen and R' is hydrogen, the formula represents a "formate". In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

As used herein, the term "nitro" means —$NO_2$; the term "halogen" designates —F, —C, —Br, or —I; the term "sulfhydryl" means —SH; the term "hydroxyl" means-OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

Described herein are devices for determining or monitoring the quality of a food product. The devices described herein includes a low-cost and hydrophobic pH-sensitive film for use as a pH-pending sensor instead of expensive and in-direct sensory instrumentation. The pH-sensitive film converts food spoilage information to easy-to-capture image information (e.g., a color map). The quick response (QR) code calibrates the color difference derived from the surrounding environment (e.g., moisture level, light source and angle). The QR code also stores the pre-established database for classifying the food quality.

In one aspect, the QR code can be easily scanned and decoded by the users' smartphone when an appropriate application is installed. In one aspect, food quality data such as, for example, microbial counts, acetic acid content, pH value according to different storage time and temperature, can be collected and recorded in the QR code system. The relationship between the food detection film color and one or more freshness parameters can be established. In one aspect, the devices described herein can be part of or incorporated into a food packaging material. In other aspects, the device can be a stand-alone article. For example, the device can be a sticker with the QR code and pH-sensitive film that can be applied directly to the food article.

Figure 3:
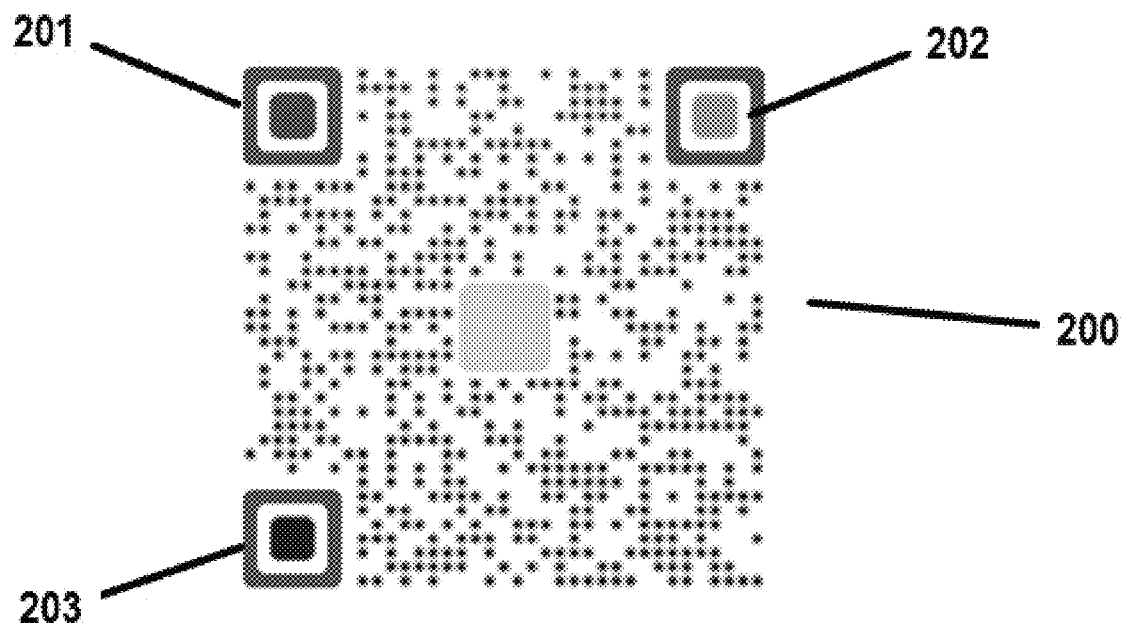
FIG. 3 shows a QR sticker as described herein.

The position of the pH-sensitive film with respect to the QR code can vary. In one aspect, the pH-sensitive film is positioned in the center of the QR code. The devices described herein include two or more different color standards. In another aspect, the device includes three different color standards, which include blue, yellow, and red. This feature of the device is depicted in FIGS. 1 and 3, where the device 200 has three color standards 201, 202, and 203 positioned at a corner of the device. The pH-sensitive film 204 is positioned at the center of the QR code. A system (e.g., smartphone application) is programmed according to the relationship between the color change and food freshness database. A camera detects the color produced by the pH-sensitive film, and the color data is calibrated by color standards in the device. In one aspect, the camera is a digital camera. In other aspects, the camera can be a smartphone camera.

The color produced by the pH-sensitive film provides chemical information (e.g., changes in pH at the surface of the food product). The chemical information is converted to numeral and verbal terms by the QR code, including but not limited to the name of the food product, date of production, date of packaging, identity of manufacturer, expiration date, pH, microbial count, shelf life, spoilage score, organic acid type and level pH, and any combination thereof.

A model can be produced and trained over time to correlate the color produced by the pH-sensitive film to several properties of the food product. For example, algorithms can be used to correlate color data and distribution produced by the pH-sensitive film with other pre-established data such as, example, pH, temperature, time, and moisture content in order to establish relationships between food quality and the storage process parameters. In certain aspects, an easy-to-operate smartphone with embedded application and database can be used in real-time food quality detection and monitoring.

The devices described herein are designed to be attached to a food product during the packaging progress and scanned by the end-user. In one aspect, a smartphone application is programmed to retrieve information from a smart phone camera. After the end-user takes a picture of the device, the smartphone application matches collected data with pre-defined machine model to classify food information into quality categories. A food quality report is then provided back to the user. For individual users, the devices described herein can be integrated into smart appliances to report the freshness of food without user scanning. For business scale, the devices can be further integrated into commercial shelf and warehouse to monitor product freshness continuously as a solution of digitalizing quality information in the food supply chain. Rather than the dependence on "best used by" and expiration dates, as well as individualistic sensory assumptions (e.g. smell and taste), the devices described herein provide an easy-to-operate, quick and real-time detection of food quality.

The dimensions of the pH-sensitive film present in the devices described herein can vary depending upon the end-use of the device. In one aspect, the pH-sensitive film has a thickness of about 5 μm to about 10 μm, or about 5 μm, about 6 μm, about 7 μm, about 8 μm, about 9 μm, or about 10 μm, where any value can be a lower and upper end-point of a range (e.g., about 5 μm to about 9 μm, about 6 μm to about 8 μm, etc.).

The pH-sensitive film is generally composed of hydrophobic components. In one aspect, the pH-sensitive film comprises nanoparticles comprising:

a hydrophobic core comprising a hydrophobic dye; and
a copolymer of a hydrophobic polymer repeat unit and a pH responsive dendrimer repeat unit.

In one aspect, the pH-sensitive film can be produced by copolymerizing a dendrimeric macromonomer with a synthetic monomer (e.g., styrene or methyl methacrylate, MMA) in the presence of hydrophobic dye via minimemulsion polymerization to prepare pH-sensitive nanoparticles with encapsulated dye. The miniemulsion can be casted in vacuum to form the pH-sensitive film.

The nanoparticles used to the produce the pH-sensitive films can have a hydrophobic core containing one or more hydrophobic active agents. The nanoparticles can also contain a copolymer of a hydrophobic polymer repeat unit and a pH responsive dendrimer repeat unit. The nanoparticles can have a diameter, or the plurality of nanoparticles can have an average diameter, that is from about 50 nm to 500 nm, from about 50 nm to 250 nm, or from about 100 nm to 250 nm at a neutral pH. The nanoparticles can be useful to release the hydrophobic active agent a specific pH while maintaining stability and integrity at an elevated pH. The nanoparticles can therefore be useful in a variety of contexts to deliver an active agent in response to a change in pH, for example in the monitoring and preventing of food spoilage. The nanoparticles can be biocompatible and or safe for human consumption.

The nanoparticles used to the produce the pH-sensitive films can have a variety of sizes adapted to the particular needs. The nanoparticles can have a diameter of about 10 nm to 1000 nm, about 20 nm to 1000 nm, about 20 nm to 900 nm, about 20 nm to 800 nm, about 30 nm to 800 nm, about 30 nm to 750 nm, about 40 nm to 750 nm, about 50 nm to 750 nm, about 50 nm to 700 nm, about 50 nm to 650 nm, about 50 nm to 600 nm, about 50 nm to 550 nm, or about 50 nm to 500 nm. In some embodiments of plurality of the nanoparticles are provided in a composition, the plurality of nanoparticles having an average diameter of about 10 nm to 1000 nm, about 20 nm to 1000 nm, about 20 nm to 900 nm, about 20 nm to 800 nm, about 30 nm to 800 nm, about 30 nm to 750 nm, about 40 nm to 750 nm, about 50 nm to 750 nm, about 50 nm to 700 nm, about 50 nm to 650 nm, about 50 nm to 600 nm, about 50 nm to 550 nm, or about 50 nm to 500 nm. The plurality of nanoparticles can be monodisperse.

The pH-sensitive film releases the hydrophobic dye in response to a change in the pH associated with food spoilage. The pH associated with food spoilage, e.g. at which the nanoparticles release the hydrophobic dye, can be about 6.8, 6.7, 6.6, 6.5, 6.4, 6.3, 6.2, 6.1, 6.0, 5.9, 5.8, 5.7, 5.6, or less. In some embodiments the nanoparticles used to the produce the pH-sensitive films release the hydrophobic dye over a pH range of about 4 to 7, about 4.5 to 7, about 5 to 7, about 5 to 6.8, about 5.5 to 6.8, about 5.6 to 6.8, about 5.6 to 6.7, about 5.6 to 6.6, about 5.8 to 6.6, or about 6.0 to 6.6. The release of the hydrophobic dye at a specific pH produces a specific color, which is ultimately used to determine and monitor the quality of the food product as discussed above.

pH Responsive Dendrimer

The nanoparticle used to the produce the pH-sensitive films can include a pH responsive dendrimer. A variety of pH responsive dendrimers can be used. The pH responsive dendrimer can have a pH responsive amine core and a branched acrylate arm. The pH responsive amine core can change shape, size, and/or confirmation is response to a change in the pH. For example, protonation of the amines on the amine core can induce structural changes in the pH responsive amine core that induce structural changes in the arms of the dendrimer.

The pH responsive dendrimer can include a pH responsive amine core. The pH responsive amine core can be any substituted or unsubstituted, linear or branched alkyl amine having two or more amine group and having from about 2 to 20, 2 to 12, 2 to 10, 2 to 8, or 2 to 6 carbon atoms. The pH responsive amine core can be a polyamine, e.g. a diamine, a triamine, or a tetramine. The pH responsive amine core can be a diamine such as ethylene diamine, propane-1,3-diamine, propane-1,2-diamine, butane-1,4-diamine, pentane-1,5-diamine, or o-phenylene diamine. In some embodiments the pH responsive amine core is ethylene diamine.

The pH responsive amine core can have a structure defined by the formula

where A is a substituted or unsubstituted, linear or branched alkyl, heteroalkyl, alkenyl, alkynyl, carbocyclic, or heterocyclic group, preferably having about 1 to 20, 1 to 15, 1 to 12, 2 to 12, 2 to 10, 2 to 8, 2 to 6, or 2 to 5 carbon atoms; and where n is an integer greater than 2, preferably from 2 to 10, 2 to 8, 2 to 6, 2 to 5, 2 to 4, 2 to 3, or wherein n is 2. R and R' can be as defined above. In some aspects, R and/or R' include an acrylate arm as described more specifically below.

The pH responsive dendrimer can include a branched acrylate arm. The branched acrylate arm can include any acrylate structure, preferably having about 6 to 30, about 6 to 25, about 8 to 25, about 8 to 20, about 10 to 20, about 10 to 15, or about 12 carbon atoms. The pH responsive dendrimer can be an acrylate formed by the esterification of acryloyl chloride with a polyol. The polyol can be, for example, ethylene glycol, propylene glycol, glycerol, 1,2-butanediol, 1,3-butanediol, pentaerythritol, malitol, sorbitol, or other small molecule polyol. The acrylate can have a structure according the formula

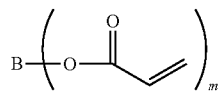

where B is a substituted or unsubstituted, linear or branched alkyl, heteroalkyl, alkenyl, alkynyl, carbocyclic, or heterocyclic group, preferably having about 1 to 20, 1 to 15, 1 to 12, 2 to 12, 2 to 10, 2 to 8, 2 to 6, or 2 to 5 carbon atoms; and where m is an integer greater than 2, preferably from 2 to 10, 2 to 8, 3 to 8, 3 to 6, 3 to 5, 3 to 4, or wherein n is 3.

The pH responsive dendrimer can have a tertiary amine core having branched acrylate arms attached thereto. For example, the pH responsive dendrimer can have a structure according to the formula

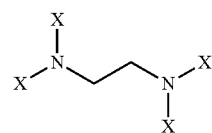

where each X is independently a branched acrylate arm, including any of the branched acrylate structures described herein. For example, each X can be a branched acrylate having from 2 to 6, 2 to 5, 2 to 4, or about 3 acrylate groups and having about 2 to 20, 2 to 12, 3 to 12, or 3 to 8 carbon atoms. In some embodiments each X is independently selected from trimethylpropane triacrylate, trimethylpropane ethoxylate triacrylate, glycerol triacrylate, glycerol ethoxylate triacrylate, and other small molecule branched acrylates.

The pH responsive dendrimer can have a structure according to the formula shown below or a derivative thereof.

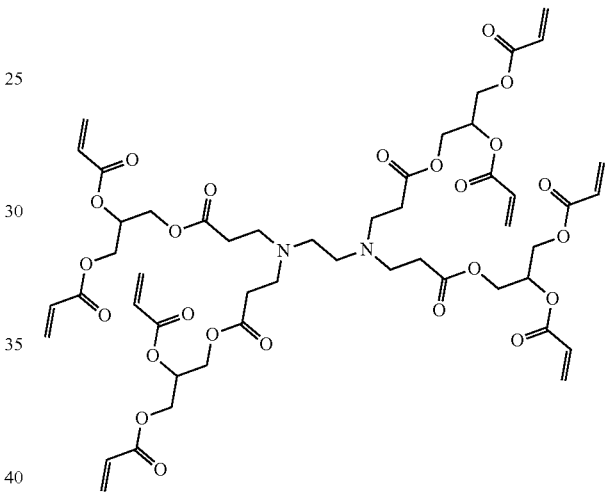

The pH responsive dendrimer can be a first-generation dendrimer, a second-generation dendrimer, a third-generation dendrimer, or higher. For example, the dendrimer can have a generation from about 1 to 10, about 1 to 8, about 1 to 6, about 1 to 5, or about 1 to 4.

Copolymers

The nanoparticle used to the produce the pH-sensitive films can include a copolymer of the pH responsive dendrimer with a hydrophobic monomer, i.e. the copolymer can contain pH responsive dendrimer repeat units and hydrophobic polymer repeat units. The copolymers can include additional repeat units. For example, the copolymers can include biodegradable polymer repeat units, hydrophobic polymer repeat units, hydrophilic polymer repeat units, stealth polymer repeat units, or the like. The copolymer can be a block copolymer or a random copolymer. The hydrophobic polymer repeat unit can be a fluorocarbon, a tetrafluoroethylene, a vinylfluoride, a siloxane, a dimethylsiloxane, butadiene, a methacrylate such as methyl methacrylate, ethylene, an olefin, styrene, propylene, or an oligomer thereof, preferably having from about 2 to 30 carbon atoms, 2 to 20 carbon atoms, 2 to 12 carbon atoms, or 2 to 10 carbon atoms. In some embodiments the hydrophobic polymer repeat unit is styrene or a derivative or oligomer thereof.

The ratio of the monomers can be used to adjust the properties such as the chemical and physical stability of the nanoparticle, and physical properties of the composite polymer film (strength and rigidity, temperature and humidity effects, stiffness and flexibility). In some embodiments the ratio (w/w) of the pH responsive dendrimer repeat unit to the hydrophobic monomer repeat unit is about 25:75, 20:80, 15:85, 10:90, or 5:95. For example, the pH responsive dendrimer repeat unit can be about 2% to 30%, about 5% to 25%, about 10% to 20%, or about 15% by weight of the copolymer.

Hydrophobic Dyes

The nanoparticles used to the produce the pH-sensitive films can release a hydrophobic dye in response to a change in the pH. When the food reaches a pH near the initiation of food spoilage, e.g. a pH of about 6.7, 6.6, 6.5, 6.4, 6.3, 6.2, 6.1, 6.0, 5.9, or 5.8, the nanoparticles can begin to release the dye as an indicator of food spoilage. Hydrophobic dyes can be organic compounds with a maximum extinction coefficient greater than 1000 L/mol/cm in the wavelength range of 400 to 750 nm and that are uncharged in aqueous solution at a pH in the range from 6 to 9. The hydrophobic dyes can be devoid of polar solubilizing groups. In some embodiments, the hydrophobic dye does not contain any sulphonic acid, carboxylic acid, or quaternary ammonium groups. The hydrophobic dye chromophore can contain an azo; methine, pyrazole napthoquinone, phthalocyanine; and, triphenylmethane chromophores. Suitable dyes can include pH indicator dyes such as Bromocresol green, Bromophenol blue, Methyl red, Ethyl orange, Solvent Blue 59, Nile red, and combinations thereof. The dye can be biocompatible and/or safe for human consumption.

Preparation of Nanoparticles

Methods of making the nanoparticles used to the produce the pH-sensitive films are provided. The methods can include miniemulsion polymerization to form the nanoparticles. The methods can include forming an oil phase containing a hydrophobic monomer, a pH responsive dendrimer, and an active agent. The methods can also include adding costabilizers to the oil phase. The methods can include sonication of the oil phase. The methods can include adding the oil phase to a water phase including the emulsifier, optionally including sonication, to form an emulsion.

The methods can include the addition of heat, light, or a catalyst to the emulsion to induce the polymerization to form the nanoparticles. The methods can include forming the emulsion at a first temperature below the polymerization temperature of the monomer and the dendrimer, followed by increasing the temperature to a second temperature above the polymerization temperature to induce the polymerization and form the nanoparticles. The first temperature can be at or around room temperature. The second temperature can be about 70° C. to 80° C., about 72° C. to 68° C., or about 73° C. to 67° C.

The methods can include adding a costabilizer or emulsifier such as modified gum Arabic, lecithin, agar, modified ghatti gum, pectin, Kara gum, xanthan gum, modified starch (especially modified food starch, e.g., modified corn starch), polyoxyethylene sorbitan, polyoxyethylene sorbitol esters (e.g. Polysorbate 20, Polysorbate 80, etc.), sugar esters, fatty alcohols (e.g., stearyl alcohol, palmityl alcohol, hexadecane-stearyl alcohol, etc.), single- and/or di-glycerides, proteins, and combinations thereof. The stabilizer can include hexadecane.

Aspect 1: A device for determining or monitoring the quality of a food product, the device comprising a pH-sensitive film incorporated within a quick response code, wherein the pH-sensitive film is positioned to be in contact with the food product, and the device further comprises at least two different color standards.

Aspect 2: The device of aspect 1, wherein the pH-sensitive film incorporated is positioned at the center of the quick response code.

Aspect 3: The device of aspect 1, wherein the device comprises at least three different color standards.

Aspect 4: The device in any one of aspects 1 to 3, wherein the standard colors comprise blue, yellow, and red.

Aspect 5: The device in any one of aspects 1 to 4, wherein the standard colors are separately positioned in a corner of the device.

Aspect 6: The device in any one of aspects 1 to 5, wherein the quick response code provides information about the food product comprising the name of the food product, date of production, date of packaging, identity of manufacturer, expiration date, pH, microbial count, shelf life, spoilage score, organic acid type and level pH, and any combination thereof.

Aspect 7: The device in any one of aspects 1 to 6, wherein the pH-sensitive film comprises nanoparticles comprising:
  a hydrophobic core comprising a hydrophobic dye; and
  a copolymer of a hydrophobic polymer repeat unit and a pH responsive dendrimer repeat unit.

Aspect 8: The device of aspect 7, wherein the hydrophobic polymer repeat unit is selected from the group consisting of styrene, methyl methacrylate, lactic acid, and a derivative thereof.

Aspect 9: The device of aspects 7 or 8, wherein the pH responsive dendrimer repeat unit has a structure according to the following formula or a derivative thereof,

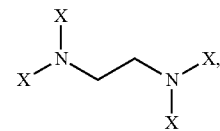

wherein each occurrence of X is independently a branched acrylate arm having a structure according to the following formula

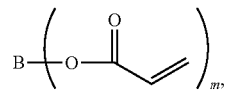

wherein each occurrence of B is a substituted or unsubstituted, linear or branched alkyl, heteroalkyl, alkenyl, alkynyl, carbocyclic, or heterocyclic group having 2 to 12 carbon atoms, wherein m is an integer of 2 to 8, wherein the pH responsive dendrimer repeat unit is present at an amount from about 5 wt % to 20 wt % based upon the weight of the copolymer, wherein the nanoparticle is chemically stable and has a diameter of about 50 nm to 200 nm at neutral pH, and
wherein the nanoparticle releases the hydrophobic dye at a pH range of about 4.5 to 6.7 to indicate the food spoilage.

Aspect 10: The device of aspects 7 or 8, wherein the pH responsive dendrimer repeat unit has a structure according to the following formula

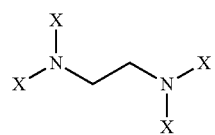

wherein each X is independently a branched acrylate arm having from 2 to 6 acrylate groups and having 2 to 20 carbon atoms.

Aspect 11: The device of aspect 10, wherein each X is independently selected from the group consisting of trimethylpropane triacrylate, trimethylpropane ethoxylate triacrylate, glycerol triacrylate, glycerol ethoxylate triacrylate, and other small molecule branched acrylates.

Aspect 12: The device of aspects 7 or 8, wherein pH responsive dendrimer repeat unit has a structure according to the following formula or a derivative thereof

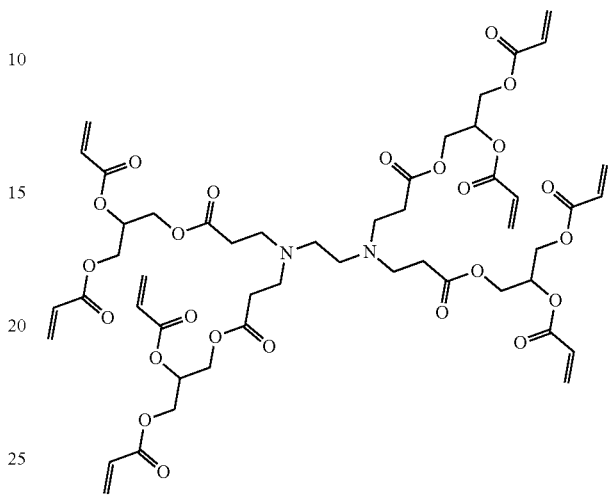

Aspect 13: The device of aspects 7 or 8, wherein pH responsive dendrimer repeat unit has a structure according to the following formula or a derivative thereof

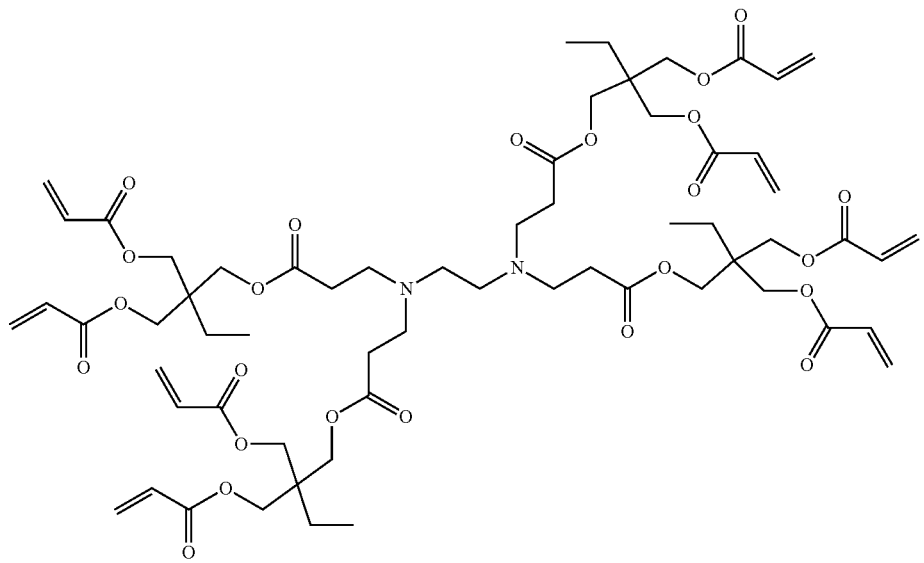

Aspect 14: The device in any one of aspects 7 to 13, wherein the hydrophobic polymer repeat unit is selected from the group consisting of a fluorocarbon, a tetrafluoroethylene, a vinylfluoride, a siloxane, a dimethylsiloxane, butadiene, a methacryate, ethylene, an olefin, styrene, propylene, and an oligomer thereof.

Aspect 15: The device in any one of aspects 1 to 6, wherein the pH-sensitive film comprises nanoparticles comprising:
a hydrophobic core comprising a hydrophobic active agent; and
a copolymer of a hydrophobic polymer repeat unit and a pH responsive dendrimer repeat unit,
wherein the pH responsive dendrimer repeat unit comprises a pH responsive amine core and a plurality of branched acrylate arms extending therefrom.

Aspect 16: The device of aspect 15, wherein the pH responsive amine core is selected from the group consisting of ethylene diamine, propane-1,3-diamine, propane-1,2-diamine, butane-1,4-diamine, pentane-1,5-diamine, and o-phenylene diamine.

Aspect 17: The device in any one of c aspects 7 to 16, wherein the nanoparticles have an average diameter of from about 50 nm to about 250 nm.

Aspect 18: The device in any one of aspects 1 to 17, wherein the pH-sensitive film has a thickness of from about 5 µm to about 10 µm.

Aspect 19: A packaged food product comprising the device in any one of aspects 1 to 18, wherein the device is in contact with the food product.

Aspect 20: The packaged food product of aspect 19, wherein the food product is selected from the group consisting of beef, pork, poultry, and fish.

Aspect 21: The packaged food product of aspect 19, wherein the packaged food product is a ready-to-eat food product.

Aspect 22: The packaged food product of aspect 19, wherein the device is part of the packaging.

Aspect 23: A method for determining the quality of a food product, the method comprising
photographing the color of the pH-sensitive film on the device in any one of aspects 1 to 18, wherein the device is in contact with the food product; and
correlating the color of the pH-sensitive film to the quality of the food product.

Aspect 24: The method of aspect 23, wherein the color of the pH-sensitive film is photographed with a digital camera.

Aspect 25: The method of aspect 23, wherein the color of the pH-sensitive film is photographed with a smartphone camera.

Aspect 26: A computing device for correlating the color produced by the pH-sensitive film in the device in any one of aspects 1 to 18 for determining the quality of a food product.

Aspect 27: The computing device of aspect 26, wherein the computing device is an application on a smart phone or tablet.

EXAMPLES

Now having described the embodiments of the present disclosure, in general, the following examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Materials and Methods
Materials & Apparatus

Pork carcass (2 lbs) after 4-h postmortem was provided from the meat processing plant of the Nettles Sausage, Co. Ltd. (Lake City, Florida). Low-density polyethylene (LDPE) lab blender bags (80-400 mL) were purchased from Fisher Scientific (USA) to homogenize pork samples within the stomacher equipment. The chemicals used for the HPLC analysis were acetonitrile, ethyl acetate, acetic (glacial) acid, which were purchased from Fisher Scientific (USA). A laboratory paddle blender (stomacher) was kindly provided by the Aquatic Food Lab Center in the Department of Food Sciences at the University of Florida (UF). To homogenize each pork sample, a laboratory paddle blender (Smasher; Microbiology International, Frederick, MD) was used to mince the sample. Following the homogenization, the supernatant of samples was obtained from a Beckman (Model J2-21) centrifuge (1375 RPM, 15 mins). The acid contents in the pork were analyzed using an Agilent Technologies 1260 Infinity LC System equipped with 1260 Quaternary G1311C pump, 1260 Infinity Standard G1329B Auto-sampler, and G1314F variable wavelength UV detector (VWD) coupled with G1362A refractive index detection (RID). A reversed-phase $C_{18}$ column was selected for the chromatographic separation of organic acids in the samples at different spoilage times. GoPro Fusion 360 camera used for image capture was kindly provided by the Marston Library of the University of Florida, Gainesville, FL.

Fabrication of Intelligent Film Sensors

The sensory films were prepared according to our previous work[19]. First, water-based and stable latex was prepared using the glycerol-based dendrimer copolymer encapsulated dye via mini-emulsion polymerization to form a core-shell nanostructure with the precise pH sensitivity. Then, each film from a mini-emulsion solution was cast and dried in a glass pyrex dish at 35±2° C. in an oven for 48 hrs. After complete evaporation of water content, copolymer films were cured in an oven at 130° C. for 1 h in the glass Pyrex dish to form a uniform film. The films were dried at 40° C. for 10 hrs in a vacuum oven until constant weight. After that, films were cooled to room temperature for 1 h. Film thickness was measured using a 6" digital caliper (Cen-Tech) with the accuracy of 0.001". The previous work examined the physical and mechanical properties of the pH-indicative sensory films as the food packaging materials for the protection and extension of the pork shelf-life[19,40]. The film demonstrated accurate and repetitive responses as the pH sensor from the pH range from 2.6-10 for the spoilage of pork and in buffer solutions at room temperature.

HPLC Analysis

The meat samples after 5-hrs postmortem were immediately measured for their organic acid (acetic acid) contents because at that time, the bacteria start growing and the food spoilage is initiated. After that, the pork meat was placed in two separate environments of 4° C. and 20° C. temperatures for up to 3 days. The samples at different storage times were collected and treated for both acetic acid measurement and color image collection by placing the film on the surface of the meat. To measure the acetic acid content, the pork samples at different times were treated as below. First, the pork samples (50 g) in 250 mL of deionized water were ground three times in a blender at high-speed at intervals of 5-7 seconds. To ensure homogenization, the cut pork sample (10 g) was further homogenized in sterile LDPE blender bags with 100 ml of deionized water using a laboratory smasher at 4° C. at a slow rate (500 strokes) for 120 s. The homogenized sample was then centrifuged at a rotor speed (5700×g) at a rotor temperature of 4° C. for 15 min. The supernatant of a centrifuged sample, which included both the protein and desired organic acids were extracted twice using ethyl acetate solvent, and the extracted acid (water-soluble liquid portion) was used for the high-performance liquid chromatography (HPLC) analysis to analyze pork samples for the acid content. Forty-eight pork samples were prepared and then filtered through a 0.45 µm membrane filter before the analysis. To detect the presence of organic acids, water and acetonitrile were used in the mobile phase at a 70:30 ratio (water-acetonitrile) and flushed at a flow rate of 0.5 mL/min for 20 mins before the analysis. At a wavelength of 254 nm, 20 µL of the sample was injected into HPLC to detect acetic organic acid, confirmed by the retention times of active compounds found within pork loin samples. Standard solutions of acid(s) were analyzed under similar gradient and non-gradient conditions to confirm experimental retention times and calculations based upon established standard curves. The organic acid content in the pork meat at a different time were determined as follows. Three repeated samples were used for each time point.

Determination of organic acid(s) in pork meat at different storage time

The concentration of the analyte was calculated by:

$$C = \frac{A - I}{m} \quad (1-1)$$

where, C—concentration of analyte
A—peak area of analyte
1—y-intercept of the standard curve
m—the slope of the standard curve $$(\%) \text{ Acid}(s) \text{ in pork meat} = \frac{C \times V}{10000W} \quad (1-2)$$

where, C—concentration of the analyte in a test solution
V—final makeup volume, mL
W—the weight of the meat sample used for the preparation of the test solution $$(\%) \text{Acid}(s) \text{ in analyte} = \frac{C}{C_s} \times 100 \quad (1-3)$$

where, C—concentration of the analyte in a test solution
$C_s$—the concentration of the standard pH and Color Measurements Using the Sensory Films Pork meat after 5-hr postmortem, was cut and stored in a refrigerated unit at 4° C. Two sensory films (1") were placed upon each cut sample (2"-3") at both 4° C. and 25° C. and then sealed in the LPDE bags to reduce gas diffusion and prevent potential spoilage. The two separate atmospheric conditioned samples were analyzed periodically for 72 hrs. The color of indicative films on meat samples was recorded periodically until the shelf-life of the pork loins was reached. Visual indication of color during the storage time was captured with a GoPro Fusion 360 camera at 10 s intervals for 72-96 hours to create "big data" of images as the QR coding database. The pH changes of pork meat samples stored at 4° C. and 20° C. were also monitored as a function of time. The variation of pH from pork samples were observed for 46 hours using the pH probe. For each sample, 2 g of pork was placed in 18 mL of deionized waters, vortexed for 15 seconds, and monitored periodically for the pH values. From this analysis, the changes that occurred could be associated with the stages of storage (e.g., early stage of storage and post-shelf life).

Colormap Model Establishment

Figures 2A, 2B:
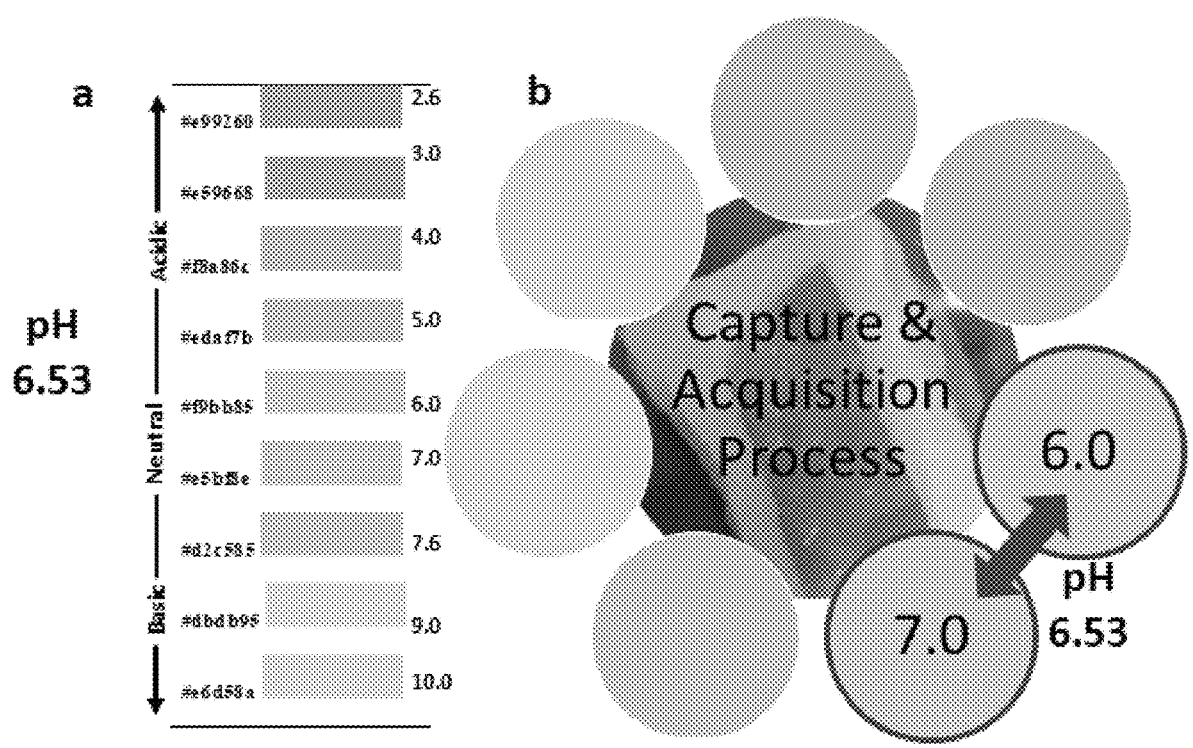
FIGS. 2A-2B shows the screen captures of the sensory film color change developed by the progressing storage time and at different pH: (a) The color captured at different pH values; (b) the acquisition process to capture the color variance of the pork lion during its storage period.

The colormaps were established from both the mini-emulsion solutions and sensory films at different pH and storage time. The color data of mini-emulsion solutions were collected by adding different pH buffer and at different sitting time. The color map of the mini-emulsion solutions in a broader pH range has been generated as the standard color database. The images of these solutions at different pH and sitting times were collected by a GoPro Camera (5760 pixels, Gainesville, FL). The color data of the sensory films were collected by recording film colors on meat (i.e., pork) surface, which were stored in a refrigerated environment (4° C.) and room temperature (20° C.), respectively. The sensory film depicts different colors by corresponding real environmental factors (i.e. pH, released acid levels, and time). All achieved color variables were converted to RGB colors using the digital camera. The RGB model uses three primary colors, red, green, and blue as an additive basis of the color model. After that, the observed color of each film was captured to construct a colormap. The linearized RBG colors at different pH and storage time were converted into a two-dimensional chromaticity space or matrix known as x (Equation 1-4) and y (Equation 1-5) using CIE (The International Commission on Illumination) 1931 XYZ color space[41]. Feasible regions of the color information were collected and averaged as a database containing all possible color responses of the sensory films. The color information represents the spoilage level of a specific food type, pork, which is non-linear, and based upon the precise pH change during the shelf-life. The acquisition process correlating the real-time pH value to color variations during the shelf life of the pork is shown in FIG. 2. By using this acquisition process and the aforementioned color conversion method, the color information is obtained at different pH range from 2.6-10.

$$x_j = \frac{X}{X + Y + Z} \quad (1-4)$$

$$y_j = \frac{Y}{X + Y + Z} \quad (1-5)$$

All data (including collected data) was randomly divided and used as training and testing data. Data collected from other literature sources were represented for the same food type (pork loin) (Table S7)[42-45] to further strengthen our model with more usable data. To obtain an accurate food spoilage classification using the sensory film color maps and machine learning method, we identified the relevant spoilage parameters (pH, acetic acid content (AA), and storage time (ST) to attribute to categories pH, AA, ST. The correlation-based feature subset selection (CFS) {pH, x, y, time, temperature}={pH, AA, ST}. In this study, to simplify the model and with the demonstration purpose, we only considered the correlation between pH, color parameters (X, Y) and the food shelf-life. The acetic acid experimental data were used for the verification purpose.

QR Code Design

A quick response (QR) code is a two dimensional and machine-readable barcode containing information about the items to which it is attached. The QR code usually consists of a black square grid on a white background, which can be quickly read by an imaging device, such as a camera, where the image can be appropriately interpreted. The QR sticker was designed to be a part of the packaging material and scanned by the end-users. The QR sticker was designed to position the sensory film in the center and three standard colors (red, blue, yellow) in the corner as shown in FIG. 3. The smartphone cameras caught the color change of the center sensory film and the color was calibrated by three standard color patches in the corner of the QR sticker (Algorithm S3). The accurate color information is enabled to represent the precise pH change that is determined by the food quality data (microbial accounts, acetic acid content, pH value according to different storage time and temperature). The relationship between the food detection film color and the aforementioned freshness parameters were established based on our experimental data and programmed into the smartphone app. This pre-set database will be used to classify the real-time food quality at any storage time based on the need of the customers.

Regression for Color Database Linearization and Food Quality Classification

When the color map corresponding to different storage time and the pH is established based on the linearized RGB color data, it is feasible to use the machine learning method (k-nearest neighbor) to predict and classify the food quality. However, in a practical case, the sensory films acting on the specific food (e.g., pork) only include the color data in a very narrow and irregular pH range (5.0-6.2). Additionally, the color data collected from the sensory films on the pork samples are shown in a non-linear relationship with the pH and the storage time, different from the data of the well-designed solution using the pH buffer. To smooth or remove excess noise from the dataset, the data smoothing method, Spline, was used to help to promote predictions and captures the important patterns from experimental trend data. Spline is a regression method that deals with non-linearity. It is used under a $3^{rd}$ order polynomial regression, where data is separated into several segments (i.e., R (red color) vs. pH) based upon each division point of measured pH (e.g., 5.4 and 5.6). To avoid overfitting in our model, the value change of parameters are allowed for certain flexibility or estimation at each data point under the smoothing of Spline. To establish a smooth regression and satisfactory R-squared value of the separated parameters, pH was rounded to one-digit decimals to increase the accuracy of regression.

When the estimation of the color map data for the sensory films was complete, the colormaps were arranged to classify the food quality of the real food type. Each data point from the experiment coupled with the film was classified by multiple labeled points on the colormap to determine the track of the shelf-life as well as the classification of quality (fresh or spoiled). The k-NN method (k-nearest neighbor) algorithm was selected to build the classification model. k-NN is a non-parametric machine learning method used for classification and regression. In this case, non-parametric machine learning is selected because the assumptions of any structure of the classification model are based upon the provided data without any further assumptions. Each data point was assigned to the most common cluster among its nearest k neighbors, and at every point, on the colormap, the data is assigned a label (in our case 0 or 1) by a plurality vote of its neighbors. We take into account the k number of neighbors based upon the outsourced collected and achieved experimental data.

Results & Discussion

Determination of the Pork Shelf-Life by Chemical Factors

The pH has been recognized as one of the main factors in determining the shelf-life of almost all food trends through its supply chain. The pH change of the perishable food during its shelf life is correlated to other factors, such as organic acid level, microbial growth, and types, storage time, storage temperature, gas levels, moisture, etc. These factors (i.e. volatile organic acid level) is useful to verify the accuracy of the pH value in determining the food quality. While food products are highly perishable during its supply chain, the food production industry has applied several preservation methods (e.g. fermentation, curing, lowering the pH, and cooking) to extend their shelf-life. Despite these efforts, various types and levels of contaminants are introduced into the perishable food upon the slaughtering process and the supply chain. Lactic acid as well as acetic acid bacteria (LAB) have shown as the primary factors that affect the spoilage of meat and meat products. Based upon its carbohydrate/amino acid metabolism, heterolactic produce significant amounts of other end products such as lactic acid, acetate, and ethanol, that are formed the "Bifidus" pathway of hexose metabolism. Besides, traditional preservation methods such as fermentation produce other organic content (i.e., acetic acid and diacetyl) from amino acids to lower the pH as well[46]. Both organic acid level and pH value during the pork loin shelf-life have been measured and recorded for food quality databases[31].

Figure 4:
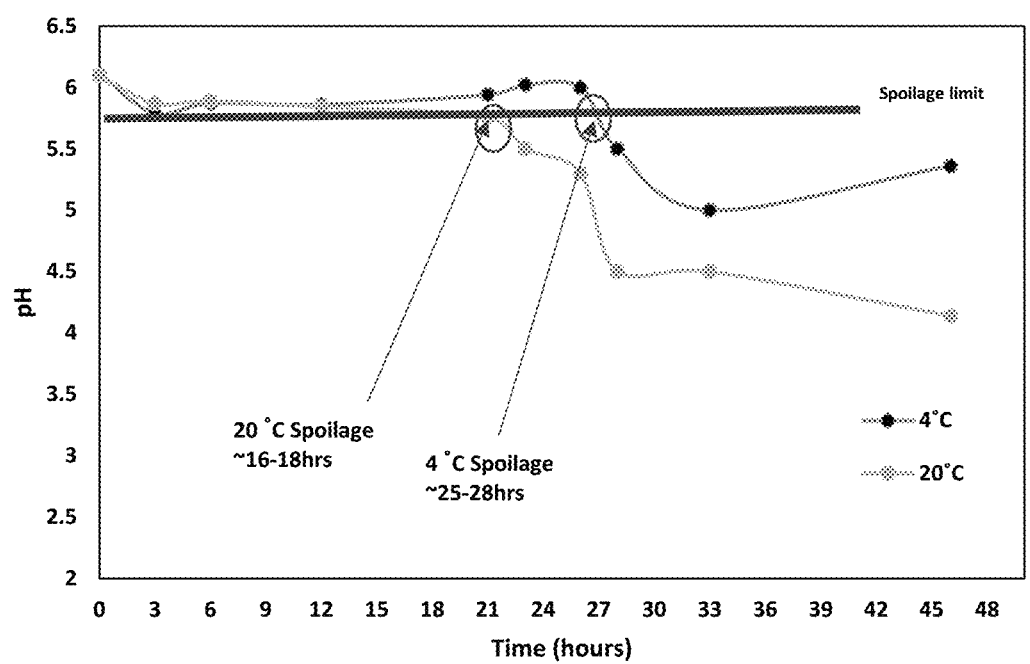
FIG. 4 shows the pH change of pork loin in storage environments with shelf-life prediction.

The variation of pH is also dependent on the muscle type, slaughter stress levels, feed type, pork color, and glucose (muscle glycogen) content before it starts the spoilage process[7,47,48]. In resting muscle, the pH can be at around 7.4. The generation of lactic acid in animals can cause pain and increase stress levels, which causes the pH to decrease to around 6.2 or as low as 5.0 under drastic circumstances. Upon slaughter, pH becomes a key determinant concerning meat quality. FIG. 4 shows the pH variations of the meat samples after slaughter during their shelf time at 20° C. and 4° C. storage temperatures, respectively. In the initiation of the analysis (time 0), the pH value of meat was around 6.2, indicating that the sample at an initial stage was a fresh and consumable meat product. At around 16-18 hrs. of storage at room temperature, the pH value was reduced to around 5.8, where this meat product was unfit for consumption[49]. After that, the pork continued to drop in pH with the range from 5.7-5.4, indicating continued spoilage[7], but the pork in the preserved temperature continued to maintain and eventually rise in pH. The pH value at 4° C. storage temperature shown in FIG. 4 proved the preservation of shelf-life at lower temperature until the storage time was around 26-33 hrs. This threshold can be used to predict and identify the shelf-life of the pork when declared unpalatable. The spoilage zone of the pork was in the pH range of 5.5-5.8, which agreed well with the previous research[7,49]. Korkeala et al (1990) investigated vacuum-packed cooked ring sausages stored at 2, 4, and 12° C.[49]. It was reported that vacuum packaged fresh meat could extend the shelf-life of fresh meats at lower pH levels (5.4-5.8) for 6 weeks rather than the pork at higher pH values (>6.0) at 3-4 week of extension[21]. It was also found that the pork meat was deemed unfit at levels of 3-4 mg lactic acid/g and pH below 5.8-5.9. Additionally, counts of bacteria had been observed to reach about $5 \times 10^7$ or $6 \times 10^7$ CFU/g at the start of a sharp change in acid levels and pH values[49]. Knox (2003) also reported the lactic acid production caused the drop in pH to about 5.4 and 5.7 for the pork loin muscle[7]. Although there was no specific regulation for the organic acid content threshold in the meat shelf-life, researchers provided the boundaries in spoilage limits for their ongoing spoilage processes[49]. The spoilage of the preserved meat was observed at around 28 hrs. and with a pH value of 5.5 at 4° C. Our results indicated that at the pH values of 5.8-5.5, the storage pork should be deemed spoiled and unfit for consumption. Additionally, meat should be limited to air exposure for no more than 16 hrs. before frozen. The refrigeration of pork (at 4° C.) can only be considered for preservation purposes within 28 hrs. of its storage time, otherwise, the pork is unfit for consumption (FIG. 4).

Figure 12:
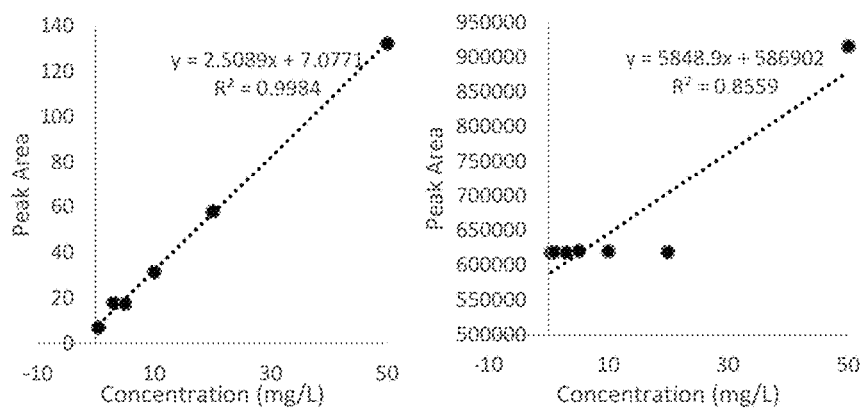
FIG. 12 shows the acid standard calibration for HPLC analysis using VWD and RID detection methods
Figure 13:
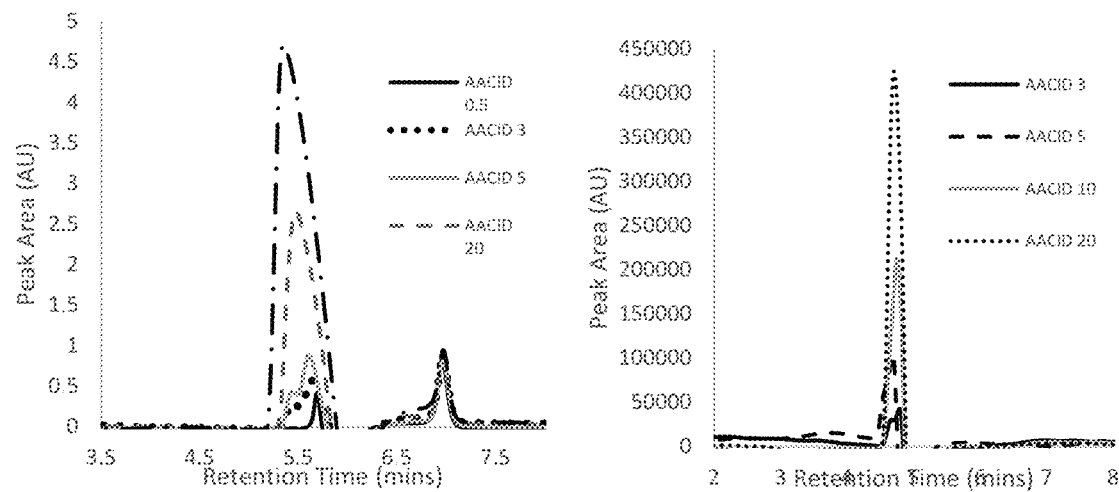
FIG. 13 shows the acetic acid standard chromatogram peaks via HPLC analysis using VWD and RID detection methods.
Figure 14:
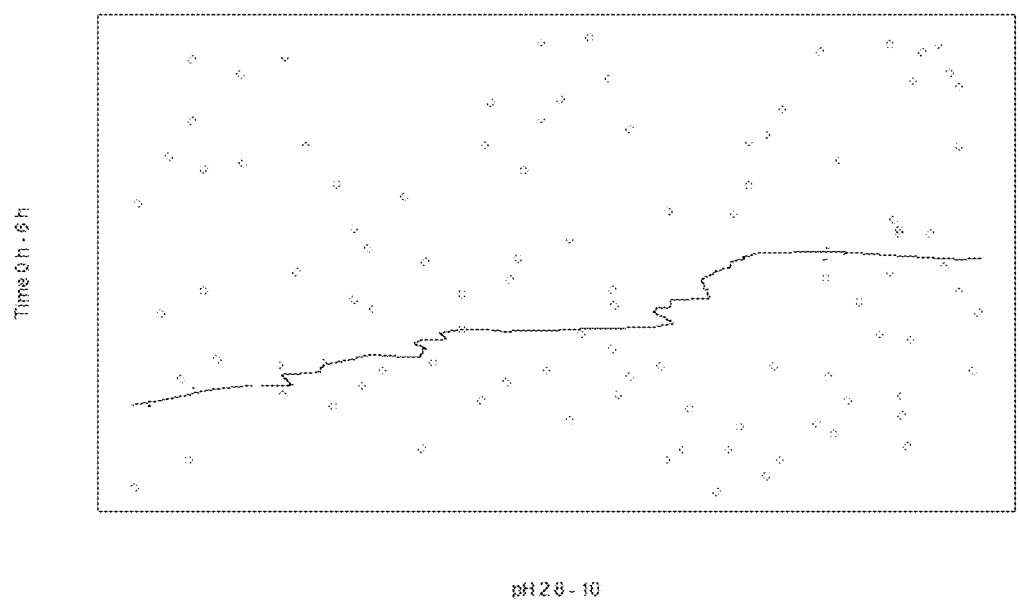
FIG. 14 shows the demonstration of food quality classification.
Figure 15:
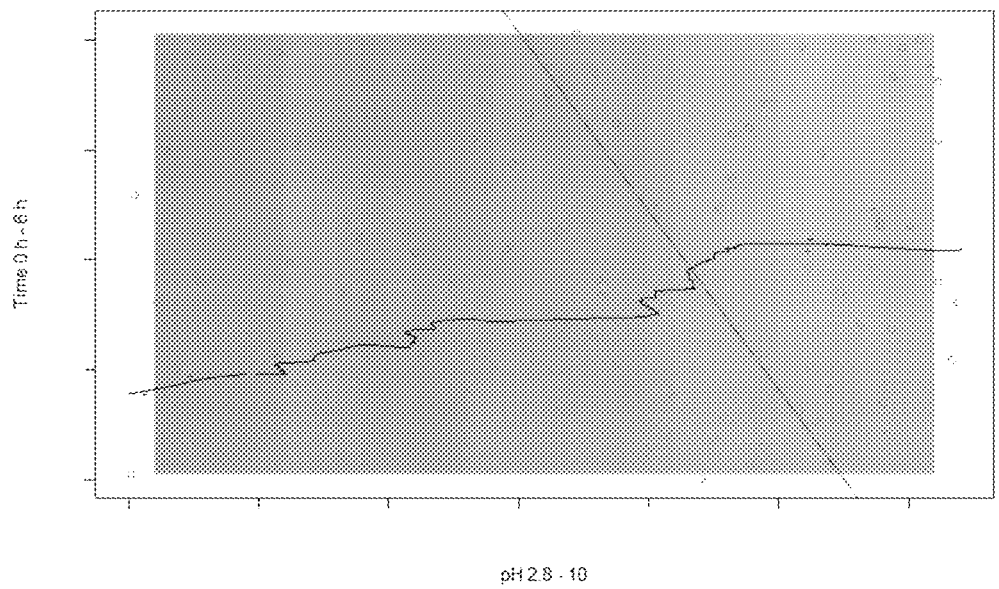
FIG. 15 shows the cross point of food decaying path (blue line) and food quality boundary (black line).

Acetic acid as a by-product from microbial bacteria behaves similarly as an indicator of food spoilage[20]. Acetic acid is the carbon source for bacteria[49], mainly lactic acid bacteria (LAB). It has been frequently associated with the genus *leuconostoc* production of organic acids[50]. Acetic acid can also be derived from amino acid degradation, hydrolysis of triglycerides[51], and heterofermentative fermentation[8,20]. Acetic acid contents in the meat samples were measured using HPLC in this study. Standard calibration of acetic acid for the HPLC measurement at known concentrations from 0.5 to 50 µg/mL are shown in the supplemental information (FIG. 12). Overall, acetic acid was observed to be accurate in the detection of various concentrations and was then used to predict the food spoilage. The HPLC analysis using the standard acetic acid samples indicated that acetic acid was more sensitive by the VWD detection than the RID detection (FIG. 13). The explanation for this is mostly due to the decrease in sensitivity using the RID method as well as its inefficiencies to detect phenolic and acidulant structures in comparison with the VWD method. Thus, we used the HPLC-VWD detection method to record the release of acetic acid from the pork samples during their shelf life.

Figure 5:
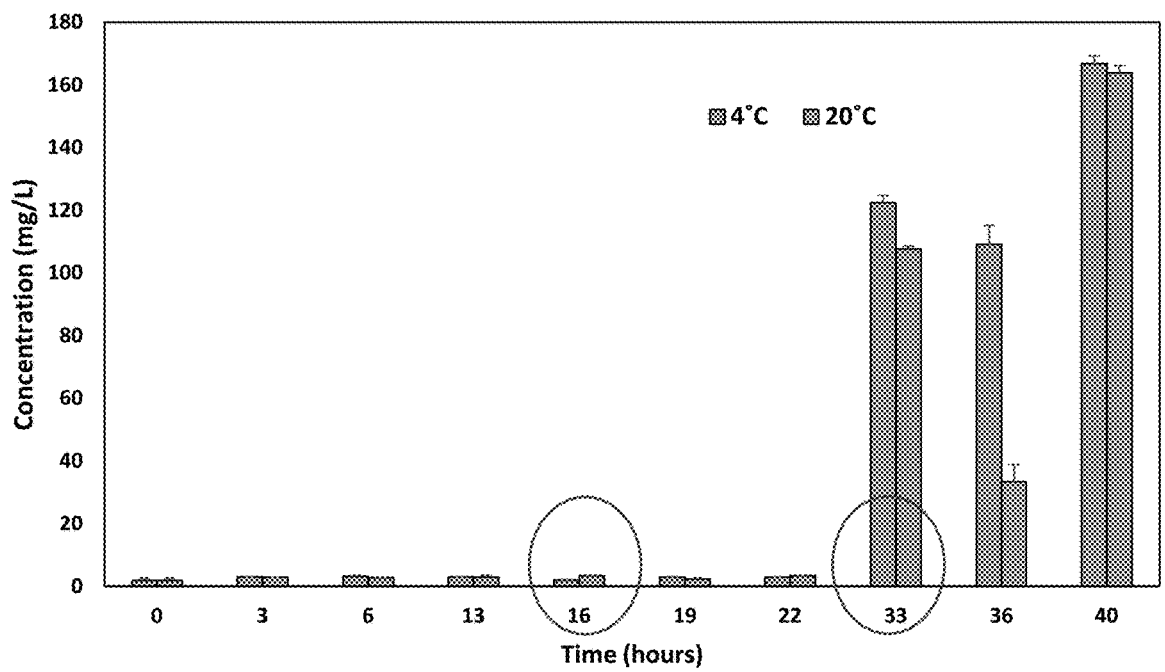
FIG. 5 shows the acetic acid level detected in pork solution using the HPLC analysis.

FIG. 5 shows the progression of acetic acid during the pork's shelf life. The initial spike of acetic acid can be explained by the exhaustion of muscle glycogen at postmortem which is best observed when oxygen and energy sources for the animal are low and/or depleted. The sustained growth of acetic acid was observed during the entire spoilage process by the continuous production of acetic acid as an end-product. The pork meat collected after 5-h post-mortem was used for the experiment. As shown in FIG. 5, the pork had the mean acetic acid concentrations of 0.024-0.036 mg/g and 0.024-0.043 mg/g upon 16-h storage time at 4° C. and 20° C. storage temperatures, respectively. After the initiation of spoilage, the air-induced meat had mean concentrations of acetic acid from 0.043-2.07 mg/g (0.0043-0.207%) from 16 to 40 hrs while the meat in the preservation environment (4° C.) ranged in the concentrations from 0.03-2.11 mg/g from 22 to 40 hrs. At these concentrations, the pork samples were on the verge of spoilage with a prediction to continue given time as a factor. The results showed that the pork meat from 5-h post-mortem had the initial indication of spoilage by producing the mean concentrations of acetic acid (2.92 mg/L and 3.4 mg/L) within a 22-33 h range and upon 16 hrs storage time at 4° C. and 20° C. storage temperatures, respectively. Similarly, as we mentioned before, the results indicated that the pH of pork meat after 28 hrs and 16 hrs was deemed unfit by pH 5.5 and 5.76 at 4° C. and 20° C. storage temperatures, respectively. During the spoilage process, the pH levels of the pork sample were comparable with the organic acid contents in samples (FIGS. 4 & 5). When meat samples were stored in air (20° C.) rather than in refrigerated temperature (4° C.), the pH was lower and the spoilage likely incurred sooner than the preserved pork sample in a lower temperature limit. The data indicated that after 16 hrs (<1 day), the sample stored at room temperature had reached its shelf-life. The sample stored at 4° C. could be considered spoiled after 33 hrs (<2 days) of storage based upon the associated pH levels of 5.5 and 4.5 as the spoilage threshold. Meanwhile, the decrease of pH values was consistent with the declaration, and the prediction of spoilage indicated by organic acid levels caused the meat deterioration as seen in both FIGS. 4 & 5. Previous research (Knox et al., 2003) also reported the organic acid production caused a drop in pH to about 5.4 and 5.7 for the pork loin muscle[7]. In ready-to-eat (RTE) meat from known manufacturers, mean concentrations of acetate ranged from 0.066-0.156%, over an 18-month period using the HPLC-UV analysis[22]. But currently, there are no specifics in the regulation of organic acid contents or bacteria levels to determine the pork shelf-life. All the experimental data showing the pH values and acetic acid levels at different storage times and temperatures were recorded in Table S5 and S6. The information presented in Table S5 feeds the classification model as well as possible boundaries to identify fresh and/or spoiled foods and food products by the value of either 1 or 0 in the following vision model and machine learning studies, respectively.

Figure 6:
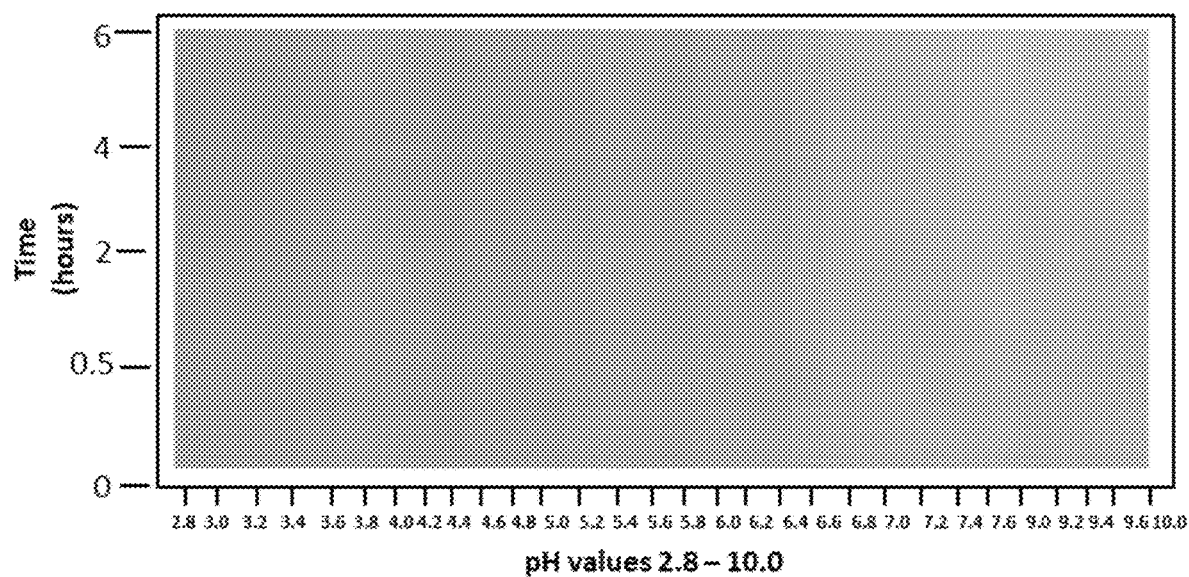
FIG. 6 shows a film solutions-based color map database.

Developed Algorithms for the Image Processing and Model Establishment Central Point Method for Image Processing The real-time color variables versus storage time using both the sensory films and the mini-emulsion solutions at the different sitting times were collected. The slow-release function of the nanoencapsulated dye could provide a smooth color distribution at a set pH range using the pH buffer, which was conducted to generate our color model for the image analysis. For the mini-emulsions, feasible regions of color variables were collected and averaged as a database containing the different sitting time at each specified pH value. A series of pH buffers were used to provide the designed pH changes. Vials containing pH buffers and the films were placed at a fixed position and recorded under consistent lighting conditions. The central-most point of each vial was captured and chosen to construct a colormap using the computational color system. The equations (1-4 and 1-5) linearized the central points into two-dimensions (i.e., x and y), which was used to be plotted versus both the pH and time (2d matrix) as shown in FIG. 6. Mini-emulsion color data from the "central points" were first converted to the computational RGB (red, green, blue) values. To create a 2-D matrix, these RGB data were further converted to an x, y, 2-D matrix relationship according to the CIE 1931 chromaticity method. Each parameter, x and y, was derived from each central-most point captured from the vials (30) containing miniemulsion solutions (Table S8). The algorithms to accomplish these conversions are shown in the SI document (Algorithm S1)[41]. Colors of each vial at different times were then extracted and saved as the response database for the following pathfinding step. To express the frame of colors from the captured images of the film, and the R environment was used to generate a 3D matrix based upon pH, RBG colors, and time. The coding for this action is expressed as Algorithm S2. Information on the system color was collected and arranged into a matrix form to provide a comprehensive description of the response on a certain type of food.

Color Matching and Correction Using the QR Code

Figure 7:
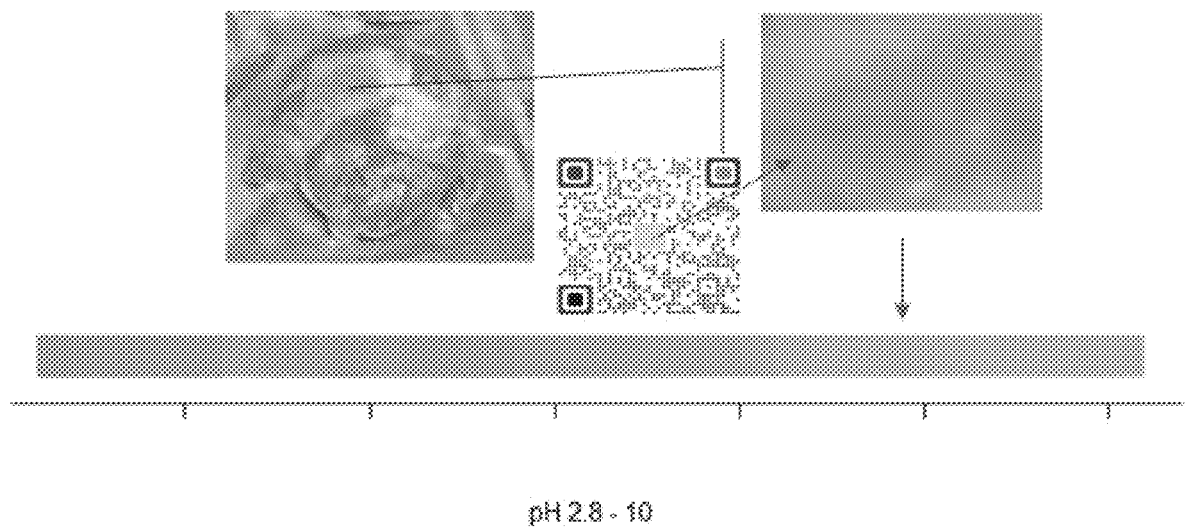
FIG. 7 shows the unique identification of color for food type (pork) from related database.

A continuous scan of film applied on a fresh analyte sample was performed and the color variations of the sensory films in real practice were recorded. Color information of the films at different times was first extracted from the video and assigned by first scanning to identify pH value. The corrected and quantitative color information after the aforementioned conversion was used to generate the color map. A path of color change was then found in the relational database to describe the behavior of the film on this particular set of scans. The path can be visualized by connecting all matched data on the color map. The path is unique to both the shelf-life and food type and may vary by the storage conditions as shown in FIG. 7, which is based upon real color along with a subsequent color adjustment in this step. The color adjustment is regulated and calibrated by our three standard color blocks located on the surface of the QR sticker to avoid outside environmental interruption (e.g., light, moisture) since the standard color and the sensory film are in the same environmental conditions.

Color Map Establishment in Practice

Figure 8:
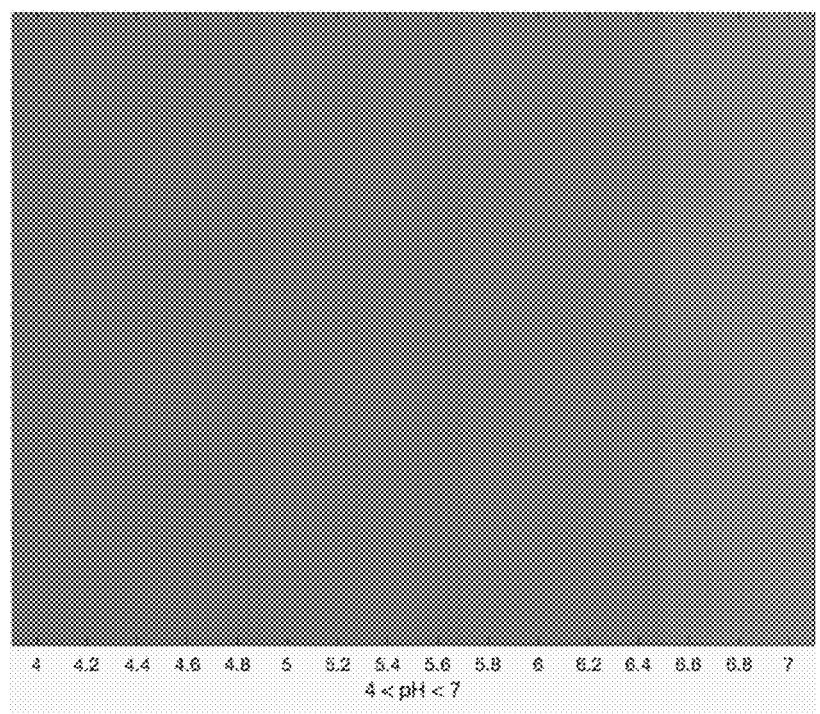
FIG. 8 shows the colormap rendered from the experimental film on pork meat.

To gather the real-time color variation data using the practical sensory films instead of the mini-emulsion solutions, we further collected the experimental data as shown in SI (Table S5 &S6). The color changes of the sensory films on the pork surfaces were recorded as a series of lapse pictures at a 10-s interval and provided the real-time pH values that corresponded to the real-time shelf life of the specific food type (e.g., pork lion). By following similar methods as the mini-emulsion solutions, the established colormap (FIG. 8) was expressed in intervals of 0.2 with one dimension to display the pH variation based upon a color change by the corresponding RGB color of the films (see Table 1). The pH value was observed to range from 5 to 6.2 during the entire shelf-life of the pork loin. To extend the color variables during a wide-range of the pH value that broadens the food types, we further expanded this database by adopting some of the mini-emulsion data with the pH value ranging from 4 to 7 (Table 1). It is necessary to find out the color relationship between the mini-emulsion and the sensory film. By comparing the color information between mini-emulsion solutions and sensory films at the known pH (5-6.2) (Table S11), we found that the difference between their RGB values can be expressed by a constant, a parameter used to determine any difference among parameters. It was determined that the testing method was mainly dependent upon the R-value rather than the other two color values. Applying this constant for the entire pH range, we expanded the color maps of the sensory films to a wide pH range, that enabled universal color maps of the sensory films, even for different food types. It is worth to mention that the color variance of the sensory film is only determined by the film properties and the pH value when we use the standard color to correct outside environmental factors (e.g., light source, moisture, etc) in the QR barcode design. Reference RGB colors were used by QR sticker color blocks. By this expansion and data inclusion, the color variation gives a more definite specific color depiction for shelf-life prediction of pork and can be therefore used to relate to wider ranges regarding the shelf-life of more food types (Algorithm S7).

TABLE 1

Estimated pH after smoothing with Spline regression tool

| pH | R | G | B |
|---|---|---|---|
| 4 | 164.63 | 107.81 | 60.27 |
| 4.2 | 167.24 | 108.11 | 59.30 |
| 4.4 | 168.61 | 109.09 | 59.90 |

TABLE 1-continued

Estimated pH after smoothing with Spline regression tool

| pH | R | G | B |
|---|---|---|---|
| 4.6 | 166.39 | 108.91 | 60.65 |
| 4.8 | 164.00 | 110.23 | 62.57 |
| 5 | 161.16 | 113.22 | 66.37 |
| 5.2 | 159.13 | 115.27 | 68.26 |
| 5.4 | 158.73 | 115.51 | 68.04 |
| 5.6 | 160.76 | 115.19 | 66.95 |
| 5.8 | 164.86 | 115.59 | 65.96 |
| 6 | 166.37 | 115.60 | 65.82 |
| 6.2 | 164.44 | 115.65 | 66.56 |
| 6.4 | 161.31 | 120.24 | 71.86 |
| 6.6 | 162.17 | 129.85 | 80.38 |
| 6.8 | 160.52 | 133.64 | 83.08 |
| 7 | 160.99 | 135.78 | 82.58 |

Film Color Trending

Figure 9:
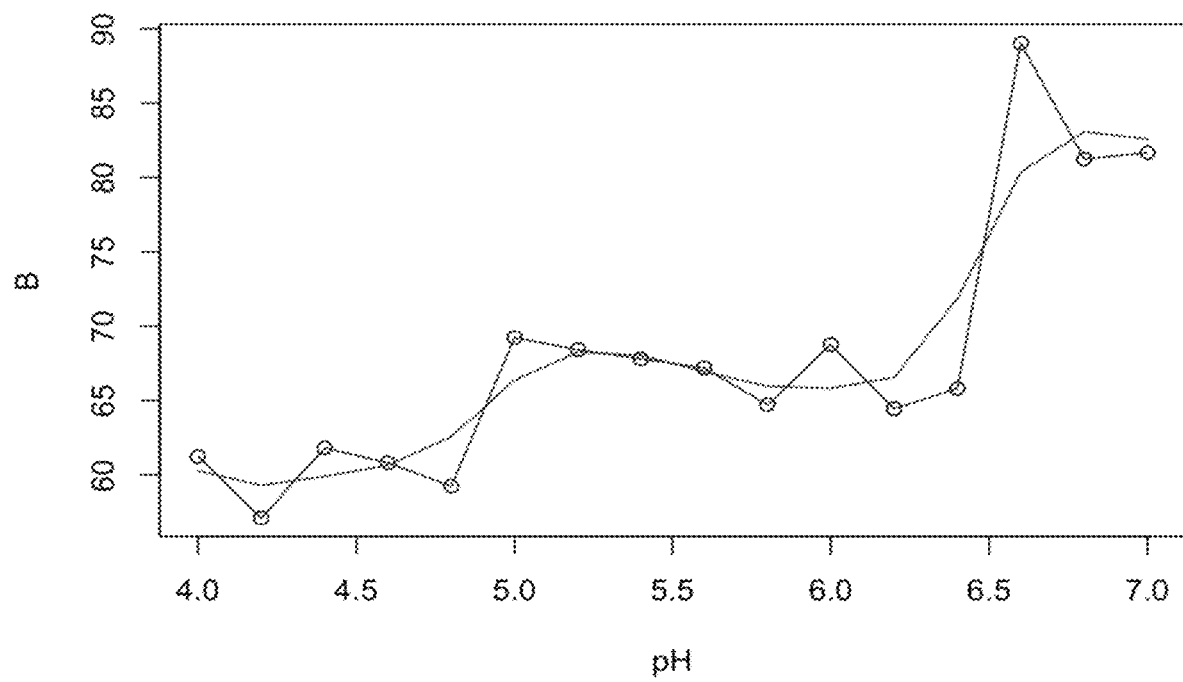
FIG. 9 shows the B factor smoothed using a Spline regression method.

In practice, the digital color information shows a nonlinear relationship with the pH value due to some errors in practical experimental measurement. To smooth the trend of changing parameters for more accurate prediction, Spline models were applied where each data parameter was separated into several segments with the data from Tables S1 & S9. As mentioned earlier, Spline is a regression tool and technique that can be used to extend models non-linearities and express the interaction between variables. Spline regression models can be used to add extra predictive data while raising the power or precision of the known predictors. In our case, the cubic Spline model is used to avoid overfitting and add precision in the model regarding various colors of RGB based upon pH values of pork loin meat from both experimental and collected data sets[10,42,43,44,45]. Also, Spline was used to estimate the gaps in our experimental data while validating the estimations and/or predictions for high accuracy where satisfactory R-squared values were derived for each color component, RGB at 0.888, 0.8948, and 0.6807, respectively. To remove the gaps of data sets and meanwhile make reliable, valid estimations and predictions, the experimental and collected data at known fixed points, such as at pH 6.0 and 5.8 with associated RGB values, were estimated using the Spline technique, which allowed the flexibility between estimations but avoided the overfitting of data which would result in added randomness instead of precision to our food quality model. This flexibility in estimation made our trend lines smoother when applied to the one-dimension colormap. The B color factor in the RGB color system is expressed as an example in FIG. 9 using the Spline regression method. The specific or fixed data (red line) known for the B factor can be seen separately from trended estimated or predicted points (blue line). This figure shows the expression of differences between both data sets to create a smoother line of trended color data for prediction purpose. With this smoothing technique, we express our overall trend of shelf-life for pork as a food type regarding the separated color factors such as B from RGB. Full trending for the estimation of RGB changes according to pH (7 to 4) is expressed in Tables S2-S4 and S12. The algorithmic expression of film color trending is given in Algorithm S8.

Food Quality Classification

Figure 10:
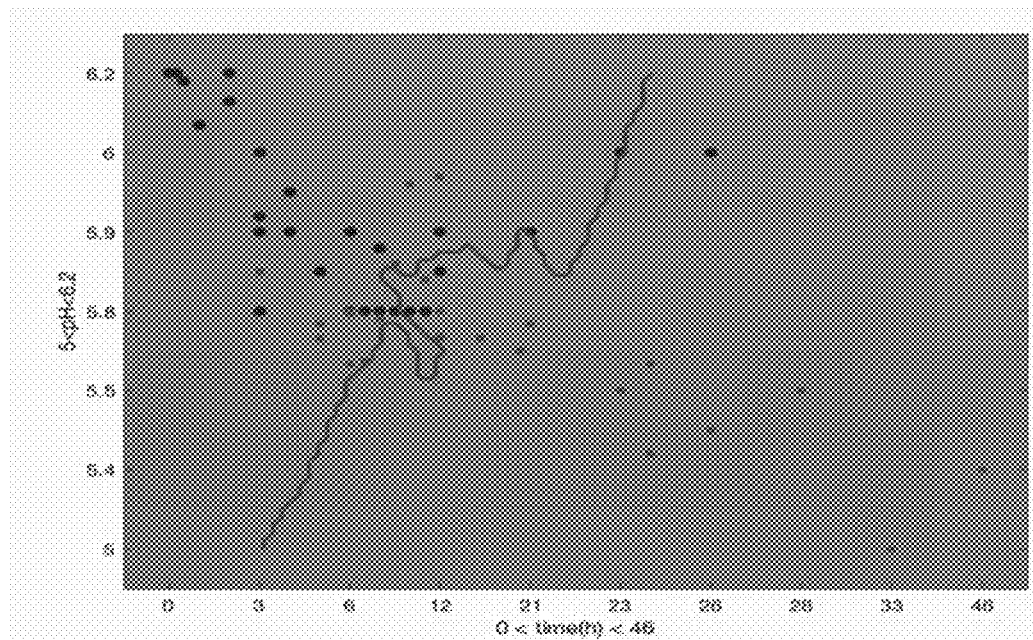
FIG. 10 shows the classification of pork loin using k-NN algorithm (k=27) at highest accuracy.
Figure 16:
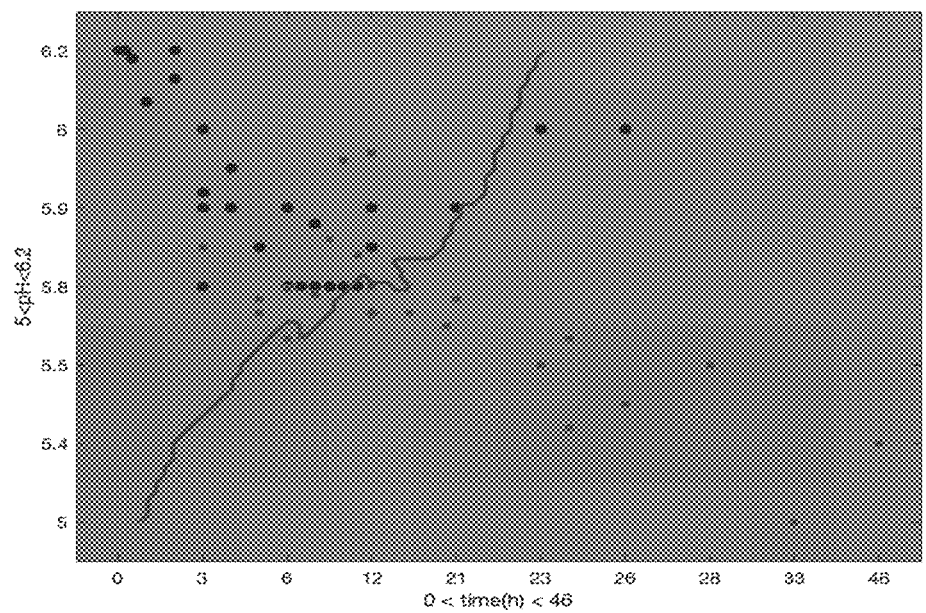
FIG. 16 shows the classification of pork shelf-life by KNN algorithm approach.
Figure 17:
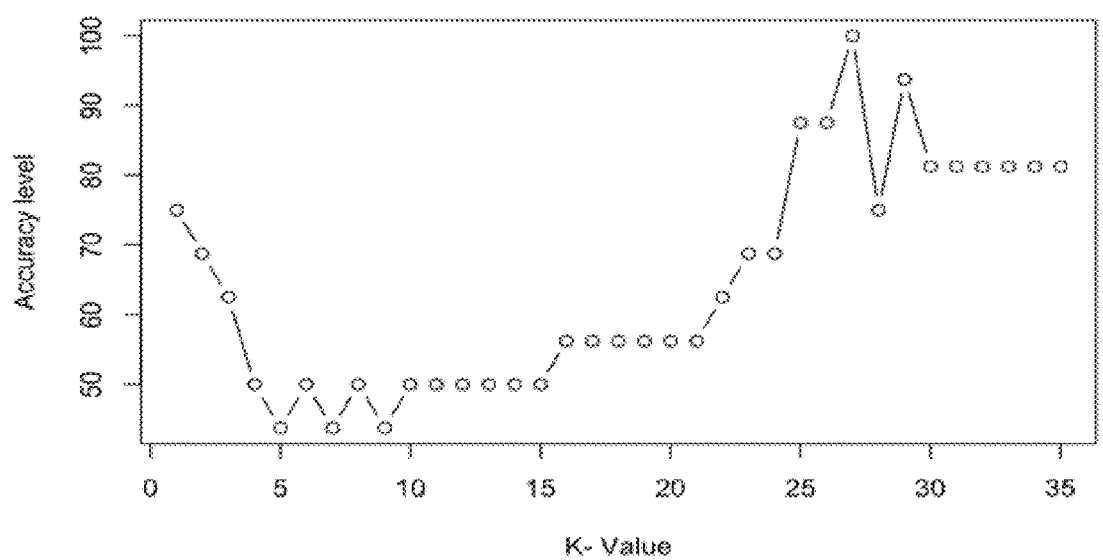
FIG. 17 shows the optimal k-Values using testing and training data for optima accuracy of data.

We further enhance this model by machine learning approaches to predict food spoilage and approximate food quality based upon the explored spoilage factors (e.g., storage time, pH value, temperature). With the pre-plotted color map, classification of food quality in the region colormap covered is needed to determine the food quality decision boundary. To demonstrate the classification problem, spoilage data was randomly divided into training and testing data, and the accuracy of classication was derived based upon the training set of data. As shown in FIG. 16, blue color dots indicate food that meets the industrial standard and red color dots indicate spoiled food. As discussed earlier, the k-nearest neighbors' algorithm (kNN) is applied to the color map region where each data point is assigned to the most common cluster among its nearest k neighbors. k-NN is a non-parametric machine learning method used for classification and regression. To decide the optimal value of k in the algorithm, a cross validation is performed on a training set of data with the separate testing data. We chose 70% of the data as the training data with varying k values from 1 to 35. And the rest 30% data was used to predict the accuracy level with different K values (FIG. 17). It was found that the highest level of accuracy is achieved when k=27. The corresponding output classification at this value of k is seen in FIG. 10 with the highest accuracy for predictions and estimations. Using the k-NN algorithm, every point on our colormap is assigned a label (in our case, 0 or 1) by a plurality of its neighbors or the data provided. A decision boundary is found to be the decaying boundary of the food that corresponds to the dataset. FIG. 10 pertains to the food type of pork loin, but this technique can be applied to other food items, such as beef (steak) or fish.

Overall QR Design

Figure 11:
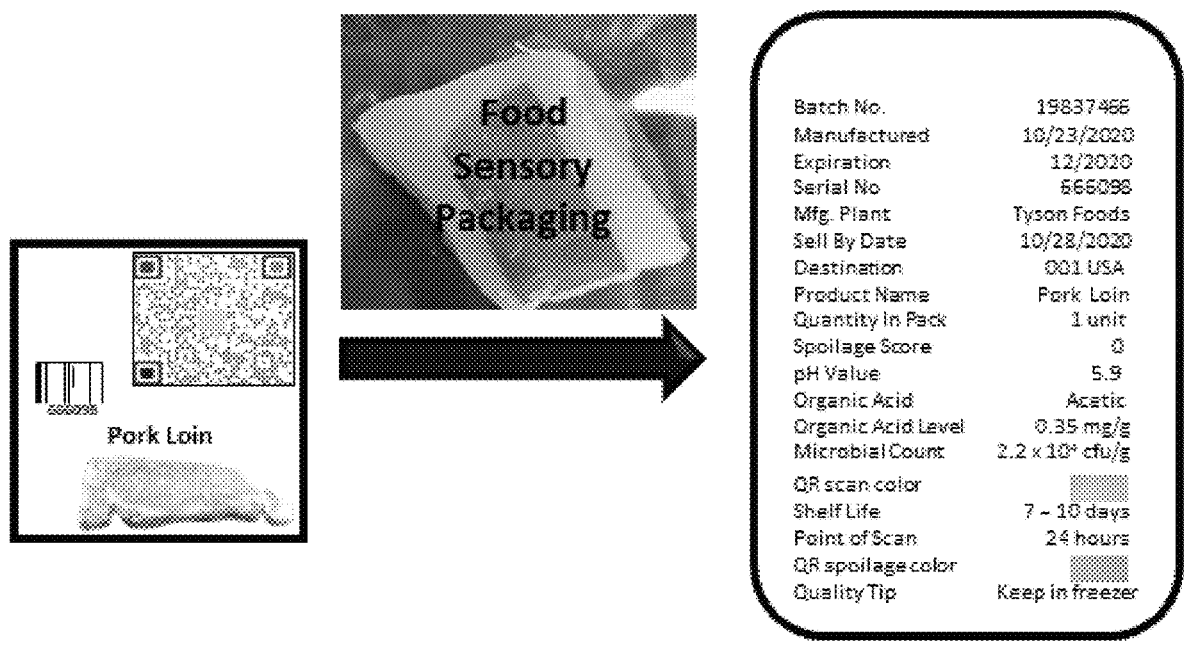
FIG. 11 shows the design of film sensor integrated QR sticker with color standards and verbal information communication.

To collect the film response data from real practice, a QR sticker design was designed to apply our sensory film on the center of the QR sticker and report the color information. The color of the film is recorded and calibrated by color standards to eliminate deviations from different lighting conditions. The function to align the colors with color scale conversion is shown in Algorithm S3. Chemical information (e.g., pH, acid level) is directly reflected by the color of the film, while the information in numeral and verbal terms is also delivered by the QR code, including but not limited to food type, date of production, and online database linkage as shown in FIG. 11. The QR sticker is designed to be attached to food during the packaging progress and scanned by the end-user. The smartphone app is programmed to pick up information using phone cameras. Users can obtain all necessary information by scanning the QR sticker with the cellphone app. with all the built-in algorithms in this study. In an event of scanning, the film and standard color blocks are located and identified. The app then matches collected data with a predefined machine learning model to classify food information into quality categories. A real-time food quality report is then provided to the user. Comparing to the readily available food packaging systems that enclose the whole of food products, using the new sensory film in the QR sticker design minimizes the production cost while the functionality remains. Analysis of color, pH, and storage time detection in various environments (e.g temperature, moisture, and oxygen levels, etc.) proved to be effective for monitoring the perishable food shelf life.

Supplemental Information

Algorithm S1. Food Quality Database in the Form of a Color Map from Color Capturing

```
getcolor <- function(x) {
    im <- load.image(x)
    centrals <- read.csv(file="centrals.csv",header=FALSE) # Define all centrals
    xradius = 10 # Define half of the x range
    yradius = 2 # Define half of the y range
    colormap <- vector( )
    for (i in 1:nrow(centrals)){
        colorR <- mean(im[(centrals[i,1]-xradius):(centrals[i,1]+xradius),(centrals[i,2]-yradius):(centrals[i,2]+yradius),1,1])
        colorG <- mean(im[(centrals[i,1]-xradius):(centrals[i,1]+xradius),(centrals[i,2]-yradius):(centrals[i,2]+yradius),1,2])
        colorB <- mean(im[(centrals[i,1]-xradius):(centrals[i,1]+xradius),(centrals[i,2]-yradius):(centrals[i,2]+yradius),1,3])
        colormap <- cbind(colormap,c(colorR,colorG,colorB))
    }
    return(colormap)}
```

Algorithm S2. Generation of 3D Matrix with Conversion of Captured Colors to RBG Colors

```
colormatrix <- array(0,c(3,30,length(file.names)))
for (i in 1:length(file.names)){
    colormatrix[,,i] <- getcolor(file.names[i])
    cat("Finished picture", i,"/", length(file.names),"\n")}
for(i in 1.length(file.names)){
    colormatrix[,,i] <- getcolor(file.names[i])
    cat("Finished picture", i,"/", length(file.names),"\n")}
```

Algorithm S3. Coding for Calibration of Film Using Standard QR Code

```
def alignImages(im1, im2):
    # Convert images to grayscale
    im1Gray = cv2.cvtColor(im1, cv2.COLOR_BGR2GRAY)
    im2Gray = cv2.cvtColor(im2, cv2.COLOR_BGR2GRAY)
    # Detect ORB features and compute descriptors.
    orb = cv2.ORB_create(MAX_FEATURES)
```

```
  keypoints1, descriptors1 = orb.detectAndCompute(im1Gray, None)
  keypoints2, descriptors2 = orb.detectAndCompute(im2Gray, None)
  # Match features.
  matcher =
cv2.DescriptorMatcher_create(cv2.DESCRIPTOR_MATCHER_BRUTEFORCE_HAMMING)
  matches = matcher.match(descriptor1, descriptors2, None)
  # Sort matches by score
  matches.sort(key=lambda x: x.distance, reverse=False)
  # Remove not so good matches
  numGoodMatches = int(len(matches) * GOOD_MATCH_PERCENT)
  matches = matches[:numGoodMatches]
  # Draw top matches
  imMatches - cv2.drawMatches(im1, keypoints1, im2, keypoints2, matches, None)
  cv2.imwrite("matches.jpg", imMatches)
  # Extract location of good matches
  points1 = np.zeros((len(matches), 2), dtype=np.float32)
  points2 = np.zeros((len(matches), 2), dtype=np.float32)
  for i, match in enumerate(matches):
     points1[i, :] = keypoints1[match.queryIdx].pt
     points2[i, :] = keypoints2[match.trainIdx].pt
  # Find homography
  h, mask = cv2.findHomography(points1, points2, cv2.RANSAC)
  # Use homography
  height, width, channels = im2.shape
  im1Reg = cv2. warpPerspective(im1, h, (width, height))
  return im1Reg, h
if_name_ == '_main_':
  # Read reference image
  retFilename = "QRstd.jpg"
  print("Reading reference image : ", refFilename)
  imReference = cv2.imread(refFilename, cv2.IMREAD_COLOR)
  #Read image to be aligned
  imFilename = "test.jpg"
  print("Reading image to align : ", imFilename)
  im = cv2.imread(imFilename, cv2.IMREAD_COLOR)
  print("Aligning images . . .")
  # Registered image will be resotred in imReg.
  # The estimated homography will be stored in h.
  imReg, h =alignImages(im, imReference)
  #Write aligned image to disk.
  outFilename = "aligned.jpg"
  print("Saving aligned image : ", outFilename";
  cv2.imwrite(outFilename, imReg)
  #Print estimated homography
  print("Estimated homography : \n", h)
       Algorithm S4. Color Matching Algorithm to Obtain the Food Decaying Path
```

```
-4635500findpH <- function(x) { #Find closest pointd<- vector( )
for (i in 1:pH) { d[i] = sqrt ((x[1]-xy[1,I,x[3]])?2 + (x[2]-xy[2,i,x[3]])?2}
return(which.min(d))}#Find path with set xy valuetestxyseries <- vector( )
result <- vector( )path <- vector( )for (i in 1:810) {
testxyseries <- c(testxv,i) result = findphlocal(testxyseries)
path <- rbind(path,c(i,result))}plot(c(0, dim(colormatrix)[2]+2),
c(0,dim(colormatric)[3]+10), type = "n", xlab="pH 2.8 - 10", ylab="Time 0 h - 6 h",
main = "colormap", xaxt="n", yaxt="n")Axis(side=1, labels=FALSE)
Axis(side=2, labels=FALSE)for (i in 10:dim(colormatrix)[3]){
for (j in 1:dim(colormatric)[2]){ rect(j, I, j+1, i+1, col = rgb(colormatrix[1,j,i],
colormatrix[2,j,i], colormatrix[3,j,i],1, maxColorValue = 1), border = NA) }}
abline(lm(path[,1]~path[,2]), col ="steelblue4", cex=2)
0findpH <- function(x) { #Find closest point
d <- vector( )
for (i in 1:pH) {
d[i] = sqrt ((x[1]-xy[1,I,x[3]])?2 + (x[2]-xy[2,i,x[3]])?2}
return(which.min(d))}
#Find path with set xy value
testxyseries <- vector( )
result <- vector( )
path <- vector( )
for (i in 1:810) {
testxyseries <- c(testxv,i)
result = findphlocal(testxyseries)
path <- rbind(path,c(i,result))}
plot(c(0, dim(colormatrix)[2]+2), c(0,dim(colormatric)[3]+10),
type = "n", xlab="pH 2.8 - 10", ylab="Time 0 h - 6 h",
main = "colormap", xaxt="n", yaxt="n")
Axis(side=1, labels=FALSE)
Axis(side=2, labels=FALSE)
for (i in 10:dim(colormatrix)[3]){
for (j in 1:dim(colormatric)[2]){
```

-continued

```
rect(j, I, j+1, i+1, col = rgb(colormatrix[1,j,i], colormatrix[2,j,i],
colormatrix[3,j,i],1, maxColorValue = 1), border = NA) }}
abline(lm(path[,1]~path[,2]), col ="steelblue4", cex=2)
```

---

Algorithm S5. Classification Algorithm in Matlab Environment for Pork Spoilage Data

```
dataR=xlsread('/Users/ellyn/Desktop/Classification2/Realigned_R.xlsx');
dataG=xlsread('/Users/ellyn/Desktop/Classification2/Realigned_G.xlsx');
dataB=xlsread('/Users/ellyn/Desktop/Classification2/Realigned_B.xlsx');
C=zeros(7,10,3);
R=dataR(2:8,2:11);
G=dataG(2:8,2:11);
B=dataB(2:8,2:11);
C(:,:,1)=R;
C(:,:,2)=G;
C(:,:,3)=B;
CC=uint8(round(C));
image(CC);
hold on;
a=[1,1;2,4;3,3;4,3;5,3;6,2;7,2;2,3;4,3.5;5/3,1;2,2;7/3,3;13/12,1.0005;4/3,33/20;
   5/3, 1.35;2,2.8;7/3,2.5;7/6,1.1;10/3,3.2;4,13/3;8/3,3.5;3,4;19/6,4;10/3,4;
   3.5,4;11/3,4;23/6,4;4,4];
b=[8,5;9,7;10,6;5,25/6;6,5;7,5.5;8/3,13/3;3,14/3;4,13/3;19/3,14/3;2,3.5;19/3,5.8;
   8/3,25/6;3,121/30;19/6,139/30;10/3,4.1;3.5,3.4;11/3,2.4;23/6,3.6;4,2.3;
   40/9,13/3;44/9,4.5;19/3,14/3];
x=[a;b];
y=[0;0;0;0;0;0;0;0;0;0;0;0;0;0;0;0;0;0;0;0;0;0;0;
   1;1;1;1;1;1;1;1;1;1;1;1;1;1;1;1;1;1;1;1;1;1;1];
N = size(x,1);
ma = {'bo','gs'};
fc = {[0 0 1],[1 0 0]};%blue vs red
yv = unique(y);
for i = 1:length(yv)
   pos = find(y==yv(i));
   plot(x(pos,1),x(pos,2),ma{i},'markerfacecolor',fc{i});
   hold on
end
[Xv, Yv] = meshgrid(min(x(:,1)):0.1:max(x(:,1)),min(x(:,2)):0.1:max(x(:,2)));
classes = zeros(size(Xv));
K = 31;
for i = 1:length(Xv(:))
   this = [Xv(i) Yv(i)]
   % calculate Euclidean distance and rank
   distances = sum((x - repmat(this,N,1)).^2,2);
   [d, I] = sort(distances,'ascend');
   [a, b]= hist(y(I(1:K)));
   pos = find(a==max(a));
   if length(pos) > 1
      order = randperm(length(pos));
      pos = pos(order(1));
   end
   classes(i) = b(pos);
end
%figure(1); hold off
for i = 1:length(yv)
   pos = find(y==yv(i));
   plot(x(pos,1),x(pos,2),ma{i},'markerfacecolor',fc{i});
   hold on
end
contour(Xv,Yv,classes,[0.5 0.5],'r','linewidth',2)
ti = sprintf('K = %g',K);
xlabel('0 < time(h) < 46');
ylabel('5<pH<6.2');
set(gca,'XTick',1:1:10);
set(gca,'XTickLabel',{'0','3','6','12','21','23','26','28','33','46'});
set(gca,'YTick',1:1:7);
set(gca,'YTickLabel',{'6.2','6','5.9','5.8','5.5','5.4','5'});
```

---

Algorithm S6. Pork Spoilage Data Colormap Coding from Sensory Film Application

```
dataR=xlsread('/Users/ellyn/Desktop/Classification2/Realigned_R.xlsx');
dataG=xlsread('/Users/ellyn/Desktop/Classification2/Realigned_G.xlsx');
dataB=xlsread('/Users/ellyn/Desktop/Classification2/Realigned_B.xlsx');
```

| Algorithm S6. Pork Spoilage Data Colormap Coding from Sensory Film Application |
| --- |
| C=zeros(7,10,3);<br>R=dataR(2:8,2:11);<br>G=dataG(2:8,2:11);<br>B=dataB(2:8,2:11);<br>C(:,:,1)=R;<br>C(:,:,2)=G;<br>C(:,:,3)=B;<br>CC=uint8(round(C));<br>image(CC);<br>xlabel('4 < pH <7');<br>%set(gca,'XTick',1:1:10);<br>%set(gca,'XTickLabel',{'0','3','6','12','21','23','26','28','33','46'});<br>%set(gca,'YTick', 1:1:7);<br>%set(gca,'YTickLabel', {'6.2','6','5.9','5.8','5.5','5.4','5'}); |

| Algorithm S7. Expanded Colormap with Pork and Miniemulsion Data |
| --- |
| data=xlsread('/Users/ellyn/Desktop/expanded/RGB_Smoothed2.xlsx');<br>C=zeros(1,16,3);<br>R=data(:,2);<br>R=reshape(R,1,16);<br>G=data(:,3);<br>G=reshape(G,1,16);<br>B=data(:,4);<br>B=reshape(B,1,16);<br>C(:,:,1)=R;<br>C(:,:,2)=G;<br>C(:,:,3)=B;<br>CC=uint8(round(C));<br>t=0:0:0;<br>image(CC);<br>xlabel('4<pH<7');<br>set(gca,'XTick',1:1:16);<br>set(gca,'XTickLabel', {'4','4.2','4.4','4.6','4.8','5','5.2','5.4','5.6','5.8','6','6.2','6.4','6.6','6.8','7'});<br>set(gca,'YTick',t); |

TABLE S1

Estimated Experimental pH After Smoothing with Spline Regression Tool

| pH | R | G | B |
| --- | --- | --- | --- |
| 5 | 160.38 | 114.33 | 69.23 |
| 5.4 | 158.87 | 115.74 | 67.80 |
| 5.6 | 157.48 | 113.57 | 67.19 |
| 5.8 | 167.91 | 116.32 | 64.73 |
| 6 | 166.26 | 117.88 | 68.76 |
| 6.2 | 168.78 | 115.10 | 64.46 |

TABLE S2

R~pH + time Regression Model

| | 0 | 3 | 6 | 12 | 21 | 23 | 26 | 28 | 33 | 46 |
| --- | --- | --- | --- | --- | --- | --- | --- | --- | --- | --- |
| 6.2 | 168.7844 | 170.074021 | 170.867403 | 170.722554 | 167.848352 | 167.034013 | 165.837262 | 165.104101 | 163.738389 | 166.531409 |
| 5.8 | 165.409822 | 168.2938 | 167.722423 | 167.577573 | 164.703372 | 163.889033 | 162.692282 | 161.95912 | 160.593409 | 163.386429 |
| 5.9 | 166.751063 | 168.270282 | 166.6188 | 168.8313 | 167.9219 | 165.230274 | 164.033523 | 163.300362 | 161.93465 | 164.72767 |
| 6 | 167.832498 | 169.351716 | 170.145099 | 170.000249 | 167.126048 | 168.0719 | 162.7968 | 164.381796 | 163.016084 | 165.809104 |
| 5.5 | 161.48011 | 162.999329 | 163.792711 | 163.647861 | 160.77366 | 159.959321 | 158.76257 | 157.4781 | 156.663697 | 159.456717 |
| 5 | 165.161101 | 166.680319 | 167.473701 | 167.328852 | 164.45465 | 163.640312 | 162.44356 | 161.710399 | 160.375 | 163.137707 |
| 5.4 | 160.752496 | 162.271715 | 163.065097 | 162.920247 | 160.046046 | 159.231707 | 158.034956 | 157.301794 | 155.936082 | 158.8688 |

TABLE S3

G~pH + time Regression Model

| | 0 | 3 | 6 | 12 | 21 | 23 | 26 | 28 | 33 | 46 |
|---|---|---|---|---|---|---|---|---|---|---|
| 6.2 | 115.0969 | 117.405575 | 119.054121 | 120.683513 | 120.36797 | 120.065085 | 119.573873 | 119.262415 | 118.74286 | 121.839037 |
| 5.8 | 111.58242 | 114.05 | 115.560711 | 117.190104 | 116.87456 | 116.571675 | 116.080463 | 115.769006 | 115.249451 | 118.345628 |
| 5.9 | 112.499575 | 114.82932 | 115.8844 | 119.0375 | 117.35 | 117.48883 | 116.997618 | 116.68616 | 116.166606 | 119.262782 |
| 6 | 113.422072 | 115.751817 | 117.400362 | 119.029755 | 118.714212 | 117.3406 | 118.9625 | 117.608657 | 117.089102 | 120.185279 |
| 5.5 | 109.38116 | 111.710905 | 113.359451 | 114.988843 | 114.6733 | 114.370415 | 113.879203 | 113.5656 | 113.048176 | 116.144367 |
| 5 | 110.655316 | 112.985061 | 114.633607 | 116.263 | 115.947456 | 115.644571 | 115.153359 | 114.841901 | 114.3281 | 117.418523 |
| 5.4 | 109.003525 | 111.33327 | 112.981816 | 114.611208 | 114.295665 | 113.99278 | 113.501568 | 113.19011 | 112.670556 | 115.7375 |

TABLE S4

B~pH + time Regression Model

| | 0 | 3 | 6 | 13 | 16 | 19 | 22 | 33 | 36 | 40 |
|---|---|---|---|---|---|---|---|---|---|---|
| 6.2 | 64.4562 | 63.6692383 | 63.471138 | 64.2364944 | 67.1919597 | 67.9745182 | 69.1393649 | 69.8783499 | 71.436358 | 71.4402652 |
| 5.8 | 64.5118385 | 63.6031 | 63.630989 | 64.3963454 | 67.3518107 | 68.1343692 | 69.2992158 | 70.0382008 | 71.5962089 | 71.6001161 |
| 5.9 | 65.1832441 | 64.5004949 | 63.7438 | 66.8438 | 67.5375 | 68.8057748 | 69.9706214 | 70.7096064 | 72.2676145 | 72.2715217 |
| 6 | 65.4732771 | 64.7905279 | 64.5924276 | 65.357784 | 68.3132494 | 65.6813 | 73.075 | 70.9996395 | 72.5576476 | 72.5615548 |
| 5.5 | 61.6024817 | 60.9197325 | 60.7216322 | 61.4869886 | 64.4424539 | 65.2250124 | 66.3898591 | 67.1906 | 68.6868522 | 68.6907593 |
| 5 | 62.1283256 | 61.4455764 | 61.2474761 | 62.0128325 | 64.9682979 | 65.7508564 | 66.915703 | 67.654688 | 69.225 | 69.2166033 |
| 5.4 | 60.7986812 | 60.115932 | 59.9178317 | 60.6831881 | 63.6386535 | 64.421212 | 65.5860586 | 66.3250436 | 67.8830517 | 67.8031 |

TABLE S5

Data Points Under in Classification of Spoilage

| pH | Time/h | Label |
|---|---|---|
| 6.2 | 0 | 0 |
| 5.8 | 3 | 0 |
| 5.9 | 6 | 0 |
| 5.9 | 12 | 0 |
| 5.9 | 21 | 0 |
| 6 | 23 | 0 |
| 6 | 26 | 0 |
| 5.5 | 28 | 1 |
| 5.4 | 33 | 1 |
| 5 | 46 | 1 |
| 5.9 | 3 | 0 |
| 5.85 | 12 | 0 |
| 5.75 | 21 | 1 |
| 5.5 | 23 | 1 |
| 5.3 | 26 | 1 |
| 6.2 | 2 | 0 |
| 6 | 3 | 0 |
| 5.9 | 4 | 0 |
| 5.7 | 5 | 1 |
| 5.6 | 6 | 1 |
| 5.7 | 12 | 1 |
| 5.6 | 24 | 1 |
| 6.19 | 0.25 | 0 |
| 5.7 | 3 | 1 |
| 5.42 | 24 | 1 |
| 6.07 | 1 | 0 |

TABLE S5-continued

Data Points Under in Classification of Spoilage

| pH | Time/h | Label |
|---|---|---|
| 6.14 | 2 | 0 |
| 5.92 | 3 | 0 |
| 5.95 | 4 | 0 |
| 5.75 | 5 | 1 |
| 5.79 | 6 | 1 |
| 5.61 | 7 | 1 |
| 5.77 | 8 | 1 |
| 5.86 | 9 | 1 |
| 5.96 | 10 | 1 |
| 5.84 | 11 | 1 |
| 5.97 | 12 | 1 |
| 6.18 | 0.5 | 0 |
| 5.88 | 8 | 0 |
| 5.7 | 12 | 1 |
| 5.85 | 5 | 0 |
| 5.8 | 6 | 0 |
| 5.8 | 7 | 0 |
| 5.8 | 8 | 0 |
| 5.8 | 9 | 0 |
| 5.8 | 10 | 0 |
| 5.8 | 11 | 0 |
| 5.8 | 12 | 0 |
| 5.7 | 16 | 1 |
| 5.65 | 20 | 1 |
| 5.6 | 24 | 1 |

TABLE S6

Pork Loin Shelf-life Classification by Spoilage Factors

| Time Hours | pH 4° C. | pH 20° C. | Time Hours | Acetic Acid Level (mg/L) 4° C. | Acetic Acid Level (mg/L) 20° C. | Classify (frsh-1 or spld-0) pH 4° C. | Classify (frsh-1 or spld-0) pH 20° C. | Classify (frsh-1 or spld-0) Acid 4° C. | Classify (frsh-1 or spld-0) Acid 20° C. |
|---|---|---|---|---|---|---|---|---|---|
| 0 | 6.2 | 6.2 | 0 | 1.92 | 1.92 | 1 | 1 | 1 | 1 |
| 3 | 5.79 | 5.87 | 3 | 2.96 | 2.839 | 1 | 1 | 1 | 1 |
| 6 | 5.87 | 5.89 | 6 | 3.2 | 2.76 | 1 | 1 | 1 | 1 |
| 12 | 5.86 | 5.84 | 13 | 2.92 | 2.88 | 1 | 1 | 1 | 1 |
| 21 | 5.94 | 5.76 | 16 | 1.96 | 3.4 | 1 | 0 | 1 | 1 |
| 23 | 6.02 | 5.5 | 19 | 2.88 | 2.28 | 1 | 0 | 1 | 0 |
| 26 | 6.00 | 5.3 | 22 | 2.84 | 3.36 | 1 | 0 | 1 | 0 |

TABLE S6-continued

Pork Loin Shelf-life Classification by Spoilage Factors

| Time Hours | pH 4° C. | pH 20° C. | Time Hours | Acetic Acid Level (mg/L) 4° C. | Acetic Acid Level (mg/L) 20° C. | Classify (frsh-1 or spld-0) pH 4° C. | Classify (frsh-1 or spld-0) pH 20° C. | Classify (frsh-1 or spld-0) Acid 4° C. | Classify (frsh-1 or spld-0) Acid 20° C. |
|---|---|---|---|---|---|---|---|---|---|
| 28 | 5.5 | 4.5 | 33 | 122.5 | 107.5 | 0 | 0 | 0 | 0 |
| 33 | 5.0 | 4.5 | 36 | 109.02 | 33.4 | 0 | 0 | 0 | 0 |
| 46 | 5.36 | 4.14 | 40 | 166.8 | 163.91 | 0 | 0 | 0 | 0 |
|  |  |  | 43 | 151.0 | 234.8 | 0 | 0 | 0 | 0 |
|  |  |  |  |  |  | 0 | 0 | 0 | 0 |

CONCLUSION

Herein, a quick and real-time food spoilage detection method using an easy-to-operate smartphone app was developed with the build-in food classification machine learning algorithm combining with our unique smart sensor-based QR sticker with the color correction function. The shelf life of pork and other highly perishable products depends on a variety of factors such as microbial quality, temperature, storage conditions, and time of storage. By the introduction of the new QR sticker with the built-in sensory film, we successfully transfer the hidden food quality information (chemical and intrinsic factors) to the easy-to-detect image information. Moreover, using pork loin as the sample, the real-time chemical factors were measured for establishing the food quality database and meanwhile validating the accuracy of using the pH sensor in our real-time imaging analysis and computational methodology. In this real-time evaluation approach, pH sensitivity during the food spoilage can be enhanced by a factor of <0.2 ph range using our invented smart film sensor. The progress of food spoilage either promotes or inhibits such progress, resulting in a color change of the system representing the chemical factors of the perishable food. The reliable and digital color variations are used to display color maps that demonstrate the real-time spoilage or decay pathways of food types. The k-NN machine learning method is applied to classify the food quality using the training data from the real-time food spoilage data that can be used for any type of perishable food. Rather than the dependence on "best used by" and expiration dates, as well as individualistic sensory assumptions (e.g. smell and taste), the intelligent sensor design, the reliable image analysis, and machine learning technology provides an easy-to-operate, quick and real-time detection for food quality, which is not available for most perishable food with various spoilage factors. For individual users, it can be integrated into smart appliances (e.g., cell phone) to report the freshness of food with a simple scanning. On a business scale, it can be further integrated into commercial shelf and warehouse to monitor product freshness continuously as a solution of digitalizing quality information in the food supply chain. Given this real-time monitoring technique, we can communicate to consumers with accurate shelf-life information at various points within the entire food supply chain.

It should be emphasized that the above-described embodiments of the present disclosure are merely possible examples of implementations and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES (1) Gupta, O., Das, A. J., Hellerstein, J., & Raskar, R. (2018). Machine learning approaches for large scale classification of produce. Sci. Rep., 8(1), 5226.
(2) Nandi, C. S., Tudu, B., & Koley, C. (2016). A machine vision technique for grading of harvested mangoes based on maturity and quality. IEEE Sens. J., 16(16), 6387-6396.
(3) Iulietto, M. F., Sechi, P., Borgogni, E., & Cenci-Goga, B. T. (2015). Meat spoilage: a critical review of a neglected alteration due to ropy slime producing bacteria. Ital. J. Anim. Sci., 14(3), 4011.
(4) Kröckel, L. (2013). The role of lactic acid bacteria in safety and flavour development of meat and meat products. Lactic acid bacteria—R & D for food, health and livestock purposes. London, UK: IntechOpen, 129-52.
(5) Hernández-Macedo, M. L., Contreras-Castillo, C. J., Tsai, S. M., Da Cruz, S. H.,
Sarantopoulos, C. I. G. L., Padula, M., & Dias, C. (2012). Gases and volatile compounds associated with microorganisms in blown pack spoilage of Brazilian vacuum-packed beef. Lett. Appl. Microbiol., 55(6), 467-475.
(6) Leisner, J. J., Laursen, B. G., Prèvost, H., Drider, D., & Dalgaard, P. (2007). Carnobacterium: positive and negative effects in the environment and in foods. FEMS Microbiol. Rev., 31(5), 592-613.
(7) Knox, B. L. (2003). The Effect of Ultimate pH on the Shelf-life and Safety of Fresh Pork Loins.
(8) Nordvi, B., Langsrud, Ø., Egelandsdal, B., Slinde, E., Vogt, G., Gutierrez, M., & Olsen, E. (2007). Characterization of volatile compounds in a fermented and dried fish product during cold storage. J. Food Sci., 72(6), S373-S380.
(9) Comi, G. (2017). Spoilage of meat and fish. In The microbiological quality of food (pp. 179-210). Woodhead Publishing.
(10) Lonergan, S. (2012). Pork quality: pH decline and pork quality.
(11) Puolanne, E. (2002). Lactic acid in muscle and its effects on meat quality. In 55^<th> Annu. Recip. Meats Conf., 2002 (Vol. 55, pp. 57-62).
(12) Rosenvold, K., & Andersen, H. J. (2003). The significance of pre-slaughter stress and diet on colour and colour stability of pork. Meat Sci., 63(2), 199-209.
(13) Bueno, L., Meloni, G. N., Reddy, S. M., & Paixao, T. R. (2015). Use of plastic-based analytical device, smartphone and chemometric tools to discriminate amines. Rsc Adv., 5(26), 20148-20154.
(14) Golasz, L. B., Silva, J. D., & Silva, S. B. D. (2013). Film with anthocyaninsal as an indicator of chilled pork deterioration. Food Sci. Tech., 33, 155-162.

(15) Wojnowski, W., Majchrzak, T., Dymerski, T., Gębicki, J., & Namieśnik, J. (2017). Portable electronic nose based on electrochemical sensors for food quality assessment. *Sensors,* 17(12), 2715.

(16) Magnaghi, L. R., Capone, F., Zanoni, C., Alberti, G., Quadrelli, P., & Biesuz, R. (2020). Colorimetric Sensor Array for Monitoring, Modelling and Comparing Spoilage Processes of Different Meat and Fish Foods. *Foods,* 9(5), 684.

(17) Talat, S., Ali, F. H., & Hassan, A. H. (2019). Efficacy of Different Marination Methods on Microbial Quality of Meat. *JOBIMB,* 7(2), 35-38.

(18) Huang, H., Liu, L., & Ngadi, M. O. (2014). Recent developments in hyperspectral imaging for assessment of food quality and safety. *Sensors,* 14(4), 7248-7276.

(19) Tong, Z., & Jairam, S. (2018). U.S. patent application Ser. No. 15/863,463

(20) Heinz, G., & Hautzinger, P. (2007). Meat processing technology for small to medium scale producers. FAO Regional Office for Asia and the Pacific (RAP) Publications ISBN: 9789747946-99-4.

(21) United States Department of Agriculture, Food Loss and Waste. The impact of food waste. https://www.usda.gov/foodlossandwaste

(22) Ahmed, O. M., Pangloli, P., Hwang, C. A., Zivanovic, S., Wu, T., D'Souza, D., & Draughon, F. A. (2015). The occurrence of *Listeria monocytogenes* in retail ready-to-eat meat and poultry products related to the levels of acetate and lactate in the products. *Food Control,* 52, 43-48.

(23) Code of Federal Regulations. Title 21-Food and Drugs. Part184, Direct Food Substances Affirmed As Generally Recognized As Safe. The Office of the Federal Register, the U.S. National Archives and Records Administration. College Park, Maryland.

(24) Code of Federal Regulations. Title 9-Animals and Animal Products. Part 424, Preparation and Processing Operations. The Office of the Federal Register, the U.S. National Archives and Records Administration. College Park, Maryland.

(25) Andersson, R., & Hedlund, B. (1983). HPLC analysis of organic acids in lactic acid fermented vegetables. *Zeitschrift für Lebensmittel-Untersuchung und Forschung,* 176(6), 440-443.

(26) Yetisen, A. K., Martinez-Hurtado, J. L., Garcia-Melendrez, A., da Cruz Vasconcellos, F., & Lowe, C. R. (2014). A smartphone algorithm with inter-phone repeatability for the analysis of colorimetric tests. *Sensor. Actuat. B-Chem.,* 196, 156-160.

(27) Zhang, X., Lu, S., & Chen, X. (2014). A visual pH sensing film using natural dyes from Bauhinia blakeana Dunn. *Sensor. Actuat. B-Chem.,* 198, 268-273.

(28) Zheng, C., Sun, D. W., & Zheng, L. (2006). Recent developments and applications of image features for food quality evaluation and inspection-a review. *Trends Food Sci. Tech.,* 17(12), 642-655.

(29) Bennedsen, B. S., Peterson, D. L., & Tabb, A. (2005). Identifying defects in images of rotating apples. *Comput. Electron. Agr.,* 48(2), 92-102.

(30) Das, A. J., Wahi, A., Kothari, I., & Raskar, R. (2016). Ultra-portable, wireless smartphone spectrometer for rapid, non-destructive testing of fruit ripeness. *Sci. Rep.,* 6, 32504.

(31) Ramírez, H. L., Soriano, A., Gómez, S., Iranzo, J. U., & Briones, A. I. (2018). Evaluation of the Food Sniffer electronic nose for assessing the shelf life of fresh pork meat compared to physicochemical measurements of meat quality. *Eur. Food Res. Technol.,* 244(6), 1047-1055.

(32) Lopez-Ruiz, N., Curto, V. F., Erenas, M. M., Benito-Lopez, F., Diamond, D., Palma, A. J., & Capitan-Vallvey, L. F. (2014). Smartphone-based simultaneous pH and nitrite colorimetric determination for paper microfluidic devices. *Anal. Chem.,* 86(19), 9554-9562.

(33) Bao, R., Chen, W., Tang, G., Chen, H., Sun, Z., & Chen, F. (2018). Classification of fresh and processed strawberry cultivars based on quality characteristics by using support vector machine and extreme learning machine. *J. Berry Res.,* 8(2), 81-94.

(34) Barbon, S., Costa Barbon, A. P. A. D., Mantovani, R. G., & Barbin, D. F. (2018). Machine Learning Applied to Near-Infrared Spectra for Chicken Meat Classification. *J. Spectrosc.,* 2018.

(35) El-Bendary, N., El Hariri, E., Hassanien, A. E., & Badr, A. (2015). Using machine learning techniques for evaluating tomato ripeness. *Expert Syst. Appl.,* 42(4), 1892-1905.

(36) Chen, P. J., Du, Y. C., Cheng, K. A., & Po, C. Y. (2016 June). Development of a management system with RFID and QR code for matching and breeding in Taiwan pig farm. *In 2016 13th International Conference on Electrical Engineering/Electronics, Computer, Telecommunications and Information Technology (ECTI-CON)* (pp. 1-5). IEEE.

(37) Liu, Y. C., & Gao, H. M. (2016). Development and Applications of Mobile Farming Information System for Food Traceability in Health Management. In *Appl. Comput. in Medicine and Health* (pp. 244-268). Morgan Kaufmann.

(38) Kim, Y. G. and E. Woo (2016). "Consumer acceptance of a quick response (QR) code for the food traceability system: Application of an extended technology acceptance model (TAM)." *Food Res. Int.* 85:266-272.

(39) Nychas, G. J. E., E. Z. Panagou and F. Mohareb (2016). "Novel approaches for food safety management and communication." *Curr. Opin. Food Sci.* 12:13-20.

(40) Pounds, K., Jairam S., Bao, H., Meng, S., Zhang, L., Godinez, S., Savin, D., Pelletier, W., Correll M. J., Tong, Z. (2020). Glycerol-based Dendrimer Nanocomposite Film As a Tunable pH-Sensor for Food Packaging. *ACS Appl. Mater Interfaces*

(41) Smith, T., & Guild, J. (1931). The CIE colorimetric standards and their use. *Transactions of the optical society,* 33(3), 73

(42) Boler, D. D., Dilger, A. C., Bidner, B. S., Carr, S. N., Eggert, J. M., Day, J. W., . . . & Killefer, J. (2010). Ultimate pH explains variation in pork quality traits. *Journal of Muscle Foods,* 21(1), 119-130.

(43) Tomović, V. M., Petrović, L. S., & Džinić, N. R. (2008). Effects of rapid chilling of carcasses and time of deboning on weight loss and technological quality of pork semimembranosus muscle. *Meat Science,* 80(4), 1188-1193.

(44) Manalo, M. R., & Gabriel, A. A. (2020). Changes in the physicochemical and microbiological properties of pork and chicken meats at ambient storage condition. *Scientific journal" Meat Technology",* 61(1), 44-53.

(45) Salas, R. C. D., & Mingala, C. N. (2017). Genetic factors affecting pork quality: halothane and rendement napole genes. *Animal biotechnology,* 28(2), 148-155.

(46) Sundaram, P. (2000). Delaying the spoilage of fresh and processed meats.

(47) Pexara, E. S., Metaxopoulos, J., & Drosinos, E. H. (2002). Evaluation of shelf life of cured, cooked, sliced turkey fillets and cooked pork sausages-'piroski'-stored under vacuum and modified atmospheres at +4 and +10 C. *Meat Sci.*, 62(1), 33-43.

(48) Raab, V., Bruckner, S., Beierle, E., Kampmann, Y., Petersen, B., & Kreyenschmidt, J. (2008). Generic model for the prediction of remaining shelf life in support of cold chain management in pork and poultry supply chains. *J. Chain Netw. Sci.*, 8(1), 59-73.

(49) Korkeala, H., Alanko, T., Mäkelä, P., & Lindroth, S. (1990). Lactic acid and pH as indicators of spoilage for vacuum-packed cooked ring sausages. *Int. J. Food Microbiol.*, 10(3-4), 245-253.

(50) Pothakos, V., Devlieghere, F., Villani, F., Björkroth, J., & Ercolini, D. (2015). Lactic acid bacteria and their controversial role in fresh meat spoilage. *Meat Sci.*, 109, 66-74.

(51) Montel, M. C., Masson, F., & Talon, R. (1998). Bacterial role in flavour development. *Meat Sci.*, 49, S1

We claim:

1. A device for determining or monitoring a quality of a food product, the device comprising;
   at least two different color standards;
   a quick response code;
   a pH-sensitive film incorporated within the quick response code and configured to come into contact with a food product and to produce a color indicative of a pH of the food product when the pH-sensitive film contacts the food product; and
   a system comprising a camera configured to detect the produced color wherein the system is programmed to provide a numerical pH value of the food product by calibrating the color detected by the camera by using the at least two different color standards.

2. The device of claim 1, wherein the quick response code has a central portion and the pH-sensitive film is disposed within the central portion of the quick response code.

3. The device of claim 1, wherein the at least two different color standards is at least three different color standards.

4. The device of claim 3, wherein the at least three different color standards comprise a blue color standard, a yellow color standard, and a red color standard.

5. The device claim 1, further comprising a corner wherein the at least two different color standards are separately positioned in the corner of the device.

6. The device claim 1, wherein the quick response code stores information about the food product comprising a name of the food product, a date of production, a date of packaging, an identity of manufacturer, an expiration date, a pH, a microbial count, a shelf life period, a spoilage score, an organic acid category and a level pH, or any combination thereof.

7. The device claim 1, wherein the pH-sensitive film comprises nanoparticles comprising:
   a hydrophobic core comprising a hydrophobic dye; and
   a copolymer of a hydrophobic polymer repeat unit and a pH responsive dendrimer repeat unit.

8. The device of claim 7, wherein the hydrophobic polymer repeat unit is selected from the group consisting of a styrene unit, a methyl methacrylate unit, and a lactic acid unit, or a combination thereof.

9. The device of claim 7, wherein the pH responsive dendrimer repeat unit has a chemical structure according to a first structural formula represented by:

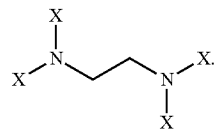

wherein each occurrence of an X arm is independently a branched acrylate arm having a chemical structure according to a second structural formula represented by:

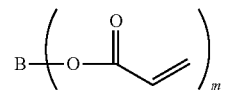

wherein each occurrence of B is an alkyl, a heteroalkyl, an alkenyl, an alkynyl, a carbocyclic, or a heterocyclic organic group having 2 to 12 carbon atoms, wherein the organic group is a substituted or a unsubstituted organic group, wherein the organic group is a linear or a branched organic group wherein m is an integer between 2 and 8, wherein the pH responsive dendrimer repeat unit is present at an amount between 5 wt % and 20 wt % based upon a weight of the copolymer, wherein the nanoparticles are chemically stable have a nanoparticle diameter between 50 nm and 200 nm at a neutral pH, and wherein the nanoparticles are configured to release the hydrophobic dye at a pH range between 4.5 and 6.7 to indicate a food spoilage.

10. The device of claim 7, wherein the pH responsive dendrimer repeat unit has a chemical structure according to a structural formula represented by:

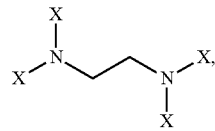

wherein each X is independently a branched acrylate arm having between 2 and 6 acrylate groups and between 2 and 20 carbon atoms.

11. The device of claim 1, wherein the pH-sensitive film comprises nanoparticles comprising:
   a hydrophobic core comprising a hydrophobic active agent;
   a copolymer of a hydrophobic polymer repeat unit; and
   a pH responsive dendrimer repeat unit, wherein the pH responsive dendrimer repeat unit comprises a pH responsive amine core and a plurality of branched acrylate arms extending from the pH responsive amine core.

12. The device of claim 7, wherein the nanoparticles have a nanoparticle diameter between 50 nm and 250 nm.

13. The device of claim 1, wherein the pH-sensitive film has a thickness between 5 μm and 10 μm.

14. A method for determining a quality of a food product, the method comprising
   photographing the color produced by a device that is in contact with the food product, wherein the device comprises at least two different color standards;

a quick response code; and a pH-sensitive film incorporated within the quick response code and configured to come into contact with the food product and to produce a color indicative of a pH of the food product when the pH-sensitive film contacts the food product; and correlating the color of the pH-sensitive film to the quality of the food product with a system comprising a camera configured to detect the produced color, wherein the system is programmed to provide a numerical pH value of the food product by calibrating the color detected by the camera by using the at least two different color standards.

15. The method of claim 14, wherein the color of the pH-sensitive film is photographed with a digital camera.

16. The method of claim 14, wherein the color of the pH-sensitive film is photographed with a smartphone camera.

17. The method of claim 14, wherein the pH-sensitive film comprises nanoparticles comprising:

a hydrophobic core comprising a hydrophobic dye; and a copolymer of a hydrophobic polymer repeat unit and a pH responsive dendrimer repeat unit.

18. The method of claim 17, wherein the pH responsive dendrimer repeat unit has a chemical structure according to a first structural formula represented by:

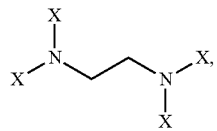

wherein each occurrence of an X arm is independently a branched acrylate arm having a chemical structure according to a second structural formula represented by:

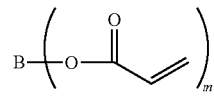

wherein each occurrence of B is an alkyl, a heteroalkyl, an alkenyl, an alkynyl, a carbocyclic, or a heterocyclic organic group having 2 to 12 carbon atoms, wherein the organic group is a substituted or a unsubstituted organic group, wherein the organic group is a linear or a branched organic group wherein m is an integer between 2 and 8, wherein the pH responsive dendrimer repeat unit is present at an amount between 5 wt % and 20 wt % based upon a weight of the copolymer, wherein the nanoparticles are chemically stable have a nanoparticle diameter between 50 nm and 200 nm at a neutral pH, and wherein the nanoparticles are configured to release the hydrophobic dye at a pH range between 4.5 and 6.7 to indicate a food spoilage.

19. The method of claim 17, wherein the pH responsive dendrimer repeat unit has a chemical structure according to a structural formula represented by:

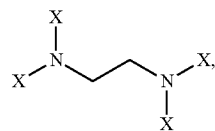

wherein each X is independently a branched acrylate arm having between 2 and 6 acrylate groups and between 2 and 20 carbon atoms.

20. The method of claim 14, wherein the pH-sensitive film comprises nanoparticles comprising:

a hydrophobic core comprising a hydrophobic active agent;

a copolymer of a hydrophobic polymer repeat unit; and a pH responsive dendrimer repeat unit, wherein the pH responsive dendrimer repeat unit comprises a pH responsive amine core and a plurality of branched acrylate arms extending from the pH responsive amine core.

* * * * *